US010517888B2

(12) United States Patent
McKenzie et al.

(10) Patent No.: US 10,517,888 B2
(45) Date of Patent: Dec. 31, 2019

(54) TREATMENT AND PREVENTION OF THROMBOSIS USING AN ANTI-MIR

(71) Applicant: THOMAS JEFFERSON UNIVERSITY, Philadelphia, PA (US)

(72) Inventors: Steven E. McKenzie, Springfield, PA (US); Yuhang Zhou, Philadelphia, PA (US); Shaji Abraham, Cherry Hill, NJ (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 0 days.

(21) Appl. No.: 15/534,410

(22) PCT Filed: Dec. 8, 2015

(86) PCT No.: PCT/US2015/064498
§ 371 (c)(1),
(2) Date: Jun. 8, 2017

(87) PCT Pub. No.: WO2016/094406
PCT Pub. Date: Jun. 16, 2016

(65) Prior Publication Data
US 2017/0360821 A1 Dec. 21, 2017

Related U.S. Application Data

(60) Provisional application No. 62/088,744, filed on Dec. 8, 2014.

(51) Int. Cl.
C12N 15/113 (2010.01)
A61K 31/7105 (2006.01)
A61K 48/00 (2006.01)
C12N 15/00 (2006.01)
A61K 31/713 (2006.01)

(52) U.S. Cl.
CPC ........ A61K 31/7105 (2013.01); A61K 31/713 (2013.01); A61K 48/00 (2013.01); C12N 15/00 (2013.01); C12N 15/113 (2013.01); C12N 2310/113 (2013.01); C12N 2310/3231 (2013.01)

(58) Field of Classification Search
None
See application file for complete search history.

(56) References Cited

U.S. PATENT DOCUMENTS

2014/0127284 A1 5/2014 Cheresh et al.

FOREIGN PATENT DOCUMENTS

WO 2011144761 A1 11/2011
WO 2012148373 A1 1/2012

OTHER PUBLICATIONS

PCT International Preliminary Report on Patentability dated Jun. 13, 2017.
International Search Report and Written Opinion of PCT/US2015/064498 dated Apr. 1, 2016.
Marquart, Tyler J. et al., "Anti-mir-33 therapy does not alter the progression of atherosclerosis in low-density lipoprotein receptor-deficient mice", Arterisclerosis, Thrombosis, and Vascular Biology, Epub. Jan. 3, 2013. vol. 33, No. 3, pp. 455-458.
Zhang, Hong et al., "Inhibition of the intrinsic coagulation pathway factor XI by antisense oligonucleotides: a novel antithrombotic strategy with lowered bleeding risk". Blood. Nov. 25, 2010. vol. 116, No. 22, pp. 4684-4693.
Zhou, Yuhang et al., "Anti-mir-148a regulates platelet FcxRIIA signaling and decreases thrombosis in vivo in mice". Blood, Epub. Oct. 29, 2015, vol. 126, No. 26, pp. 2871-2881.

Primary Examiner — J. E. Angell
(74) Attorney, Agent, or Firm — Riverside Law LLP

(57) ABSTRACT

Disclosed are anti-miR compositions and methods of use of the same for treatment of or reducing the occurrence of thrombosis and thrombosis related diseases and disorders by reducing platelet activation.

18 Claims, 33 Drawing Sheets
Specification includes a Sequence Listing.

TULA-2 mRNA

FIG. 17

| Sequence # | Description | Mibase accession | RNA Sequence |
|---|---|---|---|
| miRNA Sequence 5'--3' | | | |
| SEQ ID 1 | miR-148a-3p | MIMAT0000243 | UCAGUGCACUACAGAACUUUGU |
| SEQ ID 2 | miR-106a-5p | | AAAAGUGCUUACAGUGCAGGUAG |
| SEQ ID 3 | miR-150-5p | | UCUCCCAACCCUUGUACCAGUG |
| SEQ ID 4 | miR-199a/b-3p | MIMAT0000232 | ACAGUAGUCUGCACAUUGGUUA |
| SEQ ID 5 | miR-21-5p | MIMAT0000076 | UAGCUUAUCAGACUGAUGUUGA |
| SEQ ID 6 | miR-24-3p | MIMAT0000080 | UGGCUCAGUUCAGCAGGAACAG |
| SEQ ID 7 | miR-25-3p | MIMAT0000081 | CAUUGCACUUGUCUCGGUCUGA |
| SEQ ID 8 | miR-342-3p | MIMAT0000753 | UCUCACACAGAAAUCGCACCCGU |
| SEQ ID 9 | miR-93-5p | MIMAT0000093 | CAAAGUGCUGUUCGUGCAGGUAG |
| Anti-miR sequence 5'--3' | | | |
| SEQ ID 10 | miR-148a-3p | MIMAT0000243 | ACAAAGUUCUGUAGUGCACUGA |
| SEQ ID 11 | miR-106a-5p | | CUACCUGCACUGUAAGCACUUUU |
| SEQ ID 12 | miR-150-5p | | CACUGGUACAAGGGUUGGGAGA |
| SEQ ID 13 | miR-199a/b-3p | MIMAT0000232 | UAACCAAUGUGCAGACUACUGU |
| SEQ ID 14 | miR-21-5p | MIMAT0000076 | UCAACAUCAGUCUGAUAAGCUA |
| SEQ ID 15 | miR-24-3p | MIMAT0000080 | CUGUUCCUGCUGAACUGAGCCA |
| SEQ ID 16 | miR-25-3p | MIMAT0000081 | UCAGACCGAGACAAGUGCAAUG |
| SEQ ID 17 | miR-342-3p | MIMAT0000753 | ACGGGUGCGAUUUCUGUGUGAGA |
| SEQ ID 18 | miR-93-5p | MIMAT0000093 | CUACCUGCACGAACAGCACUUUG |
| Examples for Anti-miR-148a 5'--3' | | | |
| SEQ ID 19 | UAGUGCACUG | | |
| SEQ ID 20 | GUAGUGCACUG | | note "G" at the 3'-end of the anti-miR is complementary to "C" at position 2 of miR-148a-3p |
| SEQ ID 21 | UGUAGUGCACUG | | |
| SEQ ID 22 | CUGUAGUGCACUG | | |
| SEQ ID 23 | UCUGUAGUGCACUG | | |
| SEQ ID 24 | UUCUGUAGUGCACUG | | |
| Other Sequences 5'--3' | | | |
| SEQ ID 25 | mouse- TULA-2mRNA | | UGACAGUCACAGCUGCACUGC |
| SEQ ID 26 | Human TULA-2mRNA | | UGACAGUCAUGGCUGCACUGC |
| SEQ ID 27 | Human TULA-2mRNA | | CAAGAAGUUCAUUCUGUGCAAUA |
| SEQ ID 28 | 148MUT | | UGACAGUCAUGGCCCGCCCGC |
| Anti-miR sequences 5'--3' for Administration | | | 10-15 Nucleotide Sequence |
| SEQ ID 29 | miR-199a/b-3p | | AUGUGCAGACUACUG |
| SEQ ID 30 | miR-21-5p | | UCAGUCUGAUAAGCU |
| SEQ ID 31 | miR-24-3p | | CUGCUGAACUGAGCC |
| SEQ ID 32 | miR-25-3p | | CGAGACAAGUGCAAU |
| SED ID 33 | miR-342-3p | | CGAUUUCUGUGUGAG |
| SEQ ID 34 | miR-93-5p | | CACGAACAGCACUUU |

Rules for Anti-miR sequence design: Start with the 2nd nucleotide from the 5' end of miRNA. The anti-miR is the reverse complement from that point. The anti-miR minimum is 10-nucleotide long (underlined). Maximum 15-nucleotide long (additional 5 nucleotides are bold).

SEQUENCE LISTING

<160> NUMBER OF SEQ ID NOS: 34

<210> SEQ ID NO 1
<211> LENGTH: 22
<212> TYPE: RNA
<213> ORGANISM: Homo sapiens

<400> SEQUENCE: 1
ucagugcacu acagaacuuu gu                                      22

<210> SEQ ID NO 2
<211> LENGTH: 23
<212> TYPE: RNA
<213> ORGANISM: Homo sapiens

<400> SEQUENCE: 2
aaaagugcuu acagugcagg uag                                     23

<210> SEQ ID NO 3
<211> LENGTH: 22
<212> TYPE: RNA
<213> ORGANISM: Homo sapiens

```
<400> SEQUENCE: 3
ucucccaacc cuuguaccag ug                                          22

<210> SEQ ID NO 4
<211> LENGTH: 22
<212> TYPE: RNA
<213> ORGANISM: Homo sapiens

<400> SEQUENCE: 4
acaguagucu gcacauuggu ua                                          22

<210> SEQ ID NO 5
<211> LENGTH: 22
<212> TYPE: RNA
<213> ORGANISM: Homo sapiens

<400> SEQUENCE: 5
uagcuuauca gacugauguu ga                                          22

<210> SEQ ID NO 6
<211> LENGTH: 22
<212> TYPE: RNA
<213> ORGANISM: Homo sapiens

<400> SEQUENCE: 6
uggcucaguu cagcaggaac ag                                          22

<210> SEQ ID NO 7
<211> LENGTH: 22
<212> TYPE: RNA
<213> ORGANISM: Homo sapiens

<400> SEQUENCE: 7
cauugcacuu gucucggucu ga                                          22

<210> SEQ ID NO 8
<211> LENGTH: 23
<212> TYPE: RNA
<213> ORGANISM: Homo sapiens

<400> SEQUENCE: 8
ucucacacag aaaucgcacc cgu                                         23

<210> SEQ ID NO 9
<211> LENGTH: 23
<212> TYPE: RNA
<213> ORGANISM: Homo sapiens

<400> SEQUENCE: 9
caaagugcug uucgugcagg uag                                         23

<210> SEQ ID NO 10
<211> LENGTH: 22
<212> TYPE: RNA
<213> ORGANISM: Artificial Sequence
<220> FEATURE:
<223> OTHER INFORMATION: Designed nucleotide sequence for binding
      microRNA

<400> SEQUENCE: 10
acaaaguucu guagugcacu ga                                          22
```

```
<210> SEQ ID NO 11
<211> LENGTH: 23
<212> TYPE: RNA
<213> ORGANISM: Artificial Sequence
<220> FEATURE:
<223> OTHER INFORMATION: Designed nucleotide sequence for binding
      microRNA

<400> SEQUENCE: 11
cuaccugcac uguaagcacu uuu                                               23

<210> SEQ ID NO 12
<211> LENGTH: 22
<212> TYPE: RNA
<213> ORGANISM: Artificial Sequence
<220> FEATURE:
<223> OTHER INFORMATION: Designed nucleotide sequence for binding
      microRNA

<400> SEQUENCE: 12
cacugguaca aggguuggga ga                                                22

<210> SEQ ID NO 13
<211> LENGTH: 22
<212> TYPE: RNA
<213> ORGANISM: Artificial Sequence
<220> FEATURE:
<223> OTHER INFORMATION: Designed nucleotide sequence for binding
      microRNA

<400> SEQUENCE: 13
uaaccaaugu gcagacuacu gu                                                22

<210> SEQ ID NO 14
<211> LENGTH: 22
<212> TYPE: RNA
<213> ORGANISM: Artificial Sequence
<220> FEATURE:
<223> OTHER INFORMATION: Designed nucleotide sequence for binding
      microRNA

<400> SEQUENCE: 14
ucaacaucag ucugauaagc ua                                                22

<210> SEQ ID NO 15
<211> LENGTH: 22
<212> TYPE: RNA
<213> ORGANISM: Artificial Sequence
<220> FEATURE:
<223> OTHER INFORMATION: Designed nucleotide sequence for binding
      microRNA

<400> SEQUENCE: 15
cuguuccugc ugaacugagc ca                                                22

<210> SEQ ID NO 16
<211> LENGTH: 22
<212> TYPE: RNA
<213> ORGANISM: Artificial Sequence
<220> FEATURE:
<223> OTHER INFORMATION: Designed nucleotide sequence for binding
      microRNA

<400> SEQUENCE: 16
ucagaccgag acaagugcaa ug                                                22
```

```
<210> SEQ ID NO 17
<211> LENGTH: 23
<212> TYPE: RNA
<213> ORGANISM: Artificial Sequence
<220> FEATURE:
<223> OTHER INFORMATION: Designed nucleotide sequence for binding
      microRNA

<400> SEQUENCE: 17
acgggugcga uuucugugug aga                                              23

<210> SEQ ID NO 18
<211> LENGTH: 23
<212> TYPE: RNA
<213> ORGANISM: Artificial Sequence
<220> FEATURE:
<223> OTHER INFORMATION: Designed nucleotide sequence binding microRNA

<400> SEQUENCE: 18
cuaccugcac gaacagcacu uug                                              23

<210> SEQ ID NO 19
<211> LENGTH: 10
<212> TYPE: RNA
<213> ORGANISM: Artificial Sequence
<220> FEATURE:
<223> OTHER INFORMATION: Designed nucleotide sequence for binding
      microRNA

<400> SEQUENCE: 19
uagugcacug                                                             10

<210> SEQ ID NO 20
<211> LENGTH: 11
<212> TYPE: RNA
<213> ORGANISM: Artificial Sequence
<220> FEATURE:
<223> OTHER INFORMATION: Designed nucleotide sequence for binding
      microRNA

<400> SEQUENCE: 20
guagugcacu g                                                           11

<210> SEQ ID NO 21
<211> LENGTH: 12
<212> TYPE: RNA
<213> ORGANISM: Artificial Sequence
<220> FEATURE:
<223> OTHER INFORMATION: Designed nucleotide sequence for binding
      microRNA

<400> SEQUENCE: 21
uguagugcac ug                                                          12

<210> SEQ ID NO 22
<211> LENGTH: 13
<212> TYPE: RNA
<213> ORGANISM: Artificial Sequence
<220> FEATURE:
<223> OTHER INFORMATION: Designed nucleotide sequence for binding
      microRNA

<400> SEQUENCE: 22
cuguagugca cug                                                         13
```

```
<210> SEQ ID NO 23
<211> LENGTH: 14
<212> TYPE: RNA
<213> ORGANISM: Artificial Sequence
<220> FEATURE:
<223> OTHER INFORMATION: Designed nucleotide sequence for binding
      microRNA

<400> SEQUENCE: 23
ucuguagugc acug                                                         14

<210> SEQ ID NO 24
<211> LENGTH: 15
<212> TYPE: RNA
<213> ORGANISM: Artificial Sequence
<220> FEATURE:
<223> OTHER INFORMATION: Designed nucleotide sequence for binding
      microRNA

<400> SEQUENCE: 24
uucuguagug cacug                                                        15

<210> SEQ ID NO 25
<211> LENGTH: 21
<212> TYPE: RNA
<213> ORGANISM: Artificial Sequence
<220> FEATURE:
<223> OTHER INFORMATION: Designed nucleotide sequence for binding
      microRNA

<400> SEQUENCE: 25
ugacagucac agcugcacug c                                                 21

<210> SEQ ID NO 26
<211> LENGTH: 21
<212> TYPE: RNA
<213> ORGANISM: Artificial Sequence
<220> FEATURE:
<223> OTHER INFORMATION: Designed nucleotide sequence for binding
      microRNA

<400> SEQUENCE: 26
ugacagucau ggcugcacug c                                                 21

<210> SEQ ID NO 27
<211> LENGTH: 23
<212> TYPE: RNA
<213> ORGANISM: Artificial Sequence
<220> FEATURE:
<223> OTHER INFORMATION: Designed nucleotide sequence for binding
      microRNA

<400> SEQUENCE: 27
caagaaguuc auucugugca aua                                               23

<210> SEQ ID NO 28
<211> LENGTH: 21
<212> TYPE: RNA
<213> ORGANISM: Artificial Sequence
<220> FEATURE:
<223> OTHER INFORMATION: Designed nucleotide sequence for binding
      microRNA

<400> SEQUENCE: 28
ugacagucau ggcccgcccg c                                                 21
```

```
<210> SEQ ID NO 29
<211> LENGTH: 15
<212> TYPE: RNA
<213> ORGANISM: Artificial Sequence
<220> FEATURE:
<223> OTHER INFORMATION: Designed nucleotide sequence for binding
      microRNA

<400> SEQUENCE: 29
augugcagac uacug                                                          15

<210> SEQ ID NO 30
<211> LENGTH: 15
<212> TYPE: RNA
<213> ORGANISM: Artificial Sequence
<220> FEATURE:
<223> OTHER INFORMATION: Designed nucleotide sequence for binding
      microRNA

<400> SEQUENCE: 30
ucagucugau aagcu                                                          15

<210> SEQ ID NO 31
<211> LENGTH: 15
<212> TYPE: RNA
<213> ORGANISM: Artificial Sequence
<220> FEATURE:
<223> OTHER INFORMATION: Designed nucleotide sequence for binding
      microRNA

<400> SEQUENCE: 31
cugcugaacu gagcc                                                          15

<210> SEQ ID NO 32
<211> LENGTH: 15
<212> TYPE: RNA
<213> ORGANISM: Artificial Sequence
<220> FEATURE:
<223> OTHER INFORMATION: Designed nucleotide sequence for binding
      microRNA

<400> SEQUENCE: 32
cgagacaagu gcaau                                                          15

<210> SEQ ID NO 33
<211> LENGTH: 15
<212> TYPE: RNA
<213> ORGANISM: Artificial Sequence
<220> FEATURE:
<223> OTHER INFORMATION: Designed nucleotide sequence for binding
      microRNA

<400> SEQUENCE: 33
cgauuucugu gugag                                                          15

<210> SEQ ID NO 34
<211> LENGTH: 15
<212> TYPE: RNA
<213> ORGANISM: Artificial Sequence
<220> FEATURE:
<223> OTHER INFORMATION: Designed nucleotide sequence for binding
      microRNA

<400> SEQUENCE: 34
cacgaacagc acuuu                                                          15
```

TREATMENT AND PREVENTION OF THROMBOSIS USING AN ANTI-MIR

CROSS REFERENCE TO RELATED APPLICATIONS

This application is a National Phase Stage of International Application No. PCT/US2015/064498, filed Dec. 8, 2015, claims priority to U.S. Provisional Patent Application No. 62/088,744 filed Dec. 8, 2014, which are incorporated herein by reference in their entirety.

GOVERNMENT SUPPORT

This invention was made with government support under P01HL110860 awarded by the National Institutes of Health. The U.S. government has certain rights in the invention.

SEQUENCE LISTING

The present application contains a sequence listing, which a computer readable form (CRF) text file in compliance with 37 CFR 1.821 is submitted herewith and referenced herein in its entirety.

BACKGROUND INFORMATION

Cardiovascular disease is the leading cause of death in the developed world. Thrombosis, or blockage of a blood vessel, is the cause of (1) myocardial infarction, ischemic stroke, mesenteric arterial disease, peripheral (limb) arterial disease; (2) venous thromboembolism (deep vein thrombosis and pulmonary embolism); (3) immune-mediated thrombocytopenia and thrombosis disorders (sepsis, heparin-induced thrombocytopenia, anti-phospholipid syndrome, thrombotic thrombocytopenic purpura, thrombotic complications of therapeutic monoclonal antibodies); and (4) miscellaneous common disorders classified with the acronym MCCATS (Malformation, Cancer, Cardiac, Artificial surface, Trauma, and Sickle cell disease). Each of these four categories individually accounts for around 500,000 deaths per year in the US alone, and countless others worldwide.

Thrombosis requires formation of a platelet-fibrin plug. In short, blood cell platelets combine with the plasma coagulation factors including fibrinogen and thrombin, which clot and ultimately lead to a blockage in the vessel. This vessel could be large—an artery or vein, or smaller—an arteriole, venule, or capillary. A thrombus cannot form without the platelets being activated in the body. A common activation mechanism for platelets is activation of a protein tyrosine kinase, Syk.

Activation of platelets occurs through activation of one or more receptors on the platelet. The major classes of receptors are G protein-coupled receptors, Immunotyrosine activation motif (ITAM) receptors, and adhesion receptors among which are integrins.

The presence of cardiovascular diseases, especially thrombosis-related diseases, has resulted in the development of drugs to mitigate and treat these diseases and conditions. Prior drugs and methods of treating thrombosis focus on preventing or treating platelet activation and has centered on the molecules that turn platelets on. Cyclooxygenase, ADP receptors, thrombin receptors and the integrin αIIbβ3 turn on platelet activation. FDA-approved medicines that target them are aspirin, clopidogrel, vorapaxar and abciximab, respectively. However, as is readily known to those of skill in the art, these drugs have serious concerns in some patient populations wherein these drugs are ineffective in many patients or they cause serious bleeding. Recently, Syk has been validated as a new target to mitigate platelet activation and thrombosis[4,61].

Based on the four classes of thrombosis, the immune-mediated thrombocytopenia and thrombosis disorders present a specific opportunity as such patients are usually already in the care of physicians. Thus, there is a particular opportunity to identify and treat these patients at an early stage to reduce or eliminate morbidity. In certain cases, between about 0.1 to 3% of patients exposed to a form of the drug heparin develop heparin-induced thrombocytopenia (HIT). Patients developing HIT are at a significant risk of low platelet count and thrombosis. About 30 to 70% of untreated HIT patients develop venous or arterial thrombi that are life and/or limb threatening, which are caused by the formation of IgG antibodies against the heparin-PF4 complex. This complex activates platelets via FcγRIIA receptors, which results in thrombocytopenia and thrombosis.

Multiple Fcγ receptors for IgG antibody are present in humans. Among them, FcγRIIA, encoded by the FCGR2A gene, is the only one present on human platelets.[5] Prior studies demonstrated that platelet FcγRIIA was necessary for Heparin-induced thrombocytopenia (HIT) development in vivo with our human FcγRIIA/PF4 transgenic mouse model.[5] Binding of the Fc portion of IgG in immune complexes or cross-linking FcγRIIA promotes phosphorylation of tyrosine residues in the immunoreceptor tyrosine-base activation motifs (ITAMs), which further provides binding sites for the Src homology 2 (SH2) domains in Syk. Multiple tyrosine phosphorylation events on Syk occur after FcγRIJA ITAM phosphorylation and Syk becomes an activated protein kinase. The signaling is further transmitted by phosphorylation of phospholipase Cγ2 (PLCγ2), phosphatidylinositide 3-kinases (PI3Ks), and the Linker for Activation of T cells (LAT), followed by calcium mobilization and protein kinase C activation. These signals ultimately lead to platelet activation and thrombus formation.[7] Recently, FcγRIIA was also identified as a key regulator in platelet integrin outside-in signaling.[6,8,9] Syk is naturally regulated by platelet T-cell ubiquitin ligand 2 (TULA2). Increased TULA-2 levels will decrease Syk activity and platelet activation in thrombosis.

SUMMARY OF THE INVENTION

The present disclosure provides embodiments are related to treating and preventing thrombosis by decreasing platelet activation by using a negative regulatory mechanism via an increase in the level of a protein that is a negative regulator of platelet activation. The preferred negative regulatory mechanism uses an anti-miR to inhibit microRNA molecules to modify and regulate the production of proteins that activate or regulate thrombosis.

One method of increasing TULA-2 levels is the use of anti-miRs which target miRNAs that down-regulate TULA-2. Therefore, anti-miR compositions and methods of treatment using the same provide opportunities to treat and prevent thrombosis formation in the body. These compositions and methods can be used for prevention and treatment of thrombosis and therefore reduce the occurrence of, or treat patients suffering from myocardial infarction, ischemic stroke, mesenteric arterial disease, peripheral arterial disease, venous thromboembolism, immune-mediated thrombocytopenia and thrombosis disorders including HIT, and MCCATS disorders.

In a further embodiment, the present disclosure describes a method of treating and preventing thrombosis by decreasing platelet activation using a negative regulatory mechanism via an increase in the level of a protein that is a negative regulator of platelet activation. The method includes: (1) introducing anti-miR-148a-3p to inhibit miR-148a-3p from down regulating the mRNA encoding the T-cell ubiquitin ligand-2 (TULA-2); (2) thereby causing a subsequent increase in the amount of mRNA encoding TULA-2 and the TULA-2 protein; (3) which down regulates platelet activation; and (4) reduces or prevents thrombosis.

A further embodiment is directed to pharmaceutical compositions for use in the treatment and prevention of thrombosis. The pharmaceutical composition comprises anti-miRs to negative regulators of platelet activation, and may also comprise pharmaceutically acceptable buffer(s) or carrier(s). The anti-miRs in the pharmaceutical composition are formulated with suitable pH and salinity, for example, a pH of from 6.5 to 8.2 and a salinity of 0.5% to 0.9% NaCl, so as to be suitable for administration through any of the suitable means as described herein.

The pharmaceutical compositions of the embodiments described herein may be formulated sterile for delivery in a dose effective way to treat thrombosis. The pharmaceutical composition may be formulated for delivery as an injection or an infusion and may include a liposome, a peptide, a sugar, a nanoparticle, a synthetic molecule, a polymer, a pharmaceutically acceptable salt, or combinations thereof.

The pharmaceutical composition according to the present disclosure may be formulated for delivery by at least one route selected from the group of: infusion, intravenous, intramuscular, implantation, intraperitoneal, intradermal, intrapulmonary, parenteral, intratumoral, intravaginal, rectal, oral, buccal, topical, sublingual, intranasal, ocular, intraocular, subcutaneous, and combinations thereof.

In a further preferred embodiment is provided a kit for treating thrombosis including: a composition for treating thrombosis that is effective for decreasing platelet activation, wherein the composition is sufficiently pure for administration to a subject; a container; and instructions for use for treating thrombosis using the composition. The composition of the kit may be formulated sterile for delivery in a dose effective to treat thrombosis, and may be any of the pharmaceutical compositions described herein.

The kit of the present invention also may include an applicator for the composition, including, for example, a bottle, a sprayer, a fluid/solution dropper, an inhaler, a gauze, a strip, a brush, a syringe, or combinations thereof.

In further preferred embodiments, methods are directed to treating and preventing thrombosis due to HIT by decreasing platelet activation using a negative regulator mechanism via an increase in the level of a protein that is a negative regulator of platelet activation wherein, the method includes: (1) introducing anti-miR 148a-3p to inhibit miR 148a-3p from downregulating the mRNA encoding the protein tyrosine phosphatase ("PTP") known as TULA-2; (2) thereby causing a subsequent increase in the amount of mRNA encoding TULA-2 and the TULA-2 protein; (3) which downregulates platelet activation; and (4) reduces or prevents thrombosis.

In further embodiments, Heparin-induced thrombocytopenia is a thrombotic condition of particular concern. Accordingly, preferred methods utilize methods and compositions for the treatment and prevention of thrombosis comprising administering the anti-miR 148a-3p corresponding to SEQ ID No: 19-24 to a human patient at risk of or suffering from HIT.

A preferred embodiment comprises a method of treatment of thrombosis comprising contacting a microRNA with one or more nucleic acid molecules, wherein each of the nucleic acid molecules comprises a nucleotide sequence that is at least about 90% identical to a sequence ID NOs: 19-24 or SEQ ID NOs: 29-34.

A method for treating thrombosis comprising administering to a subject in need thereof, an effective amount of an anti-miR capable of upregulating the level of a protein that is a negative regulator of platelet activation.

A method of administering an anti-miR to a patient for reducing or treating thrombosis, comprising administering to said patient an effective amount of an anti-miR for reducing or treating thrombosis for a period of 1-21 days.

A method of reducing platelet activity in the body of a patient comprising administering to said patient, an effective amount of an anti-miR, wherein said anti-miR is capable of inhibiting a corresponding miR wherein the inhibition down regulates the mRNA encoding for TULA-2 and causing a subsequent increase in the amount of mRNA encoding TULA-2, which downregulates platelet activation.

A method for reducing the occurrence of thrombosis in a patient comprising, administering to a subject in need thereof, an effective amount of at least one anti-miR capable of upregulating TULA-2 to mediate platelet activation.

A method for reducing platelet activation comprising administering to a patient in need thereof an effective amount of an anti-miR having a corresponding miR having a binding site on TULA-2, wherein the binding of the anti-miR upregulates TULA-2 to mediate platelet activation in the body.

A method for reducing FcγRIIA-mediated thrombosis by inhibiting Syk activation by administering to a patient in need thereof an anti-miR against miRNA 148a-3p, wherein the inhibition of the miR-148a increases the TULA-2 levels in platelets in the body.

A kit for treatment of thrombosis, wherein said kit is suitable for reducing platelet activation, reducing thrombosis formation, regulating platelet activation, and/or reducing FcγRIIA-mediated thrombosis, wherein said kit comprises at least one anti-miR suitable for administration to a patient in need thereof, and instructions for treating thrombosis using the anti-miR.

Use of an anti-miR for treating thrombosis in a patient comprising administering to said patient an effective amount of an anti-miR capable of decreasing platelet activation in said patient.

Use of an anti-miR pharmaceutical composition for treating thrombosis in a patient comprising administering to said patient an effective amount of an anti-miR pharmaceutical composition capable of decreasing platelet activation in said patient.

In preferred embodiments, the pharmaceutical composition or anti-miR of any of the embodiments described above comprises one or more anti-miR have a length of between 10 and 15 nucleotides corresponding to SEQ ID Nos: 19-24 and 29-34.

In a further preferred embodiment, and of the disclosed embodiments may be combined with another embodiment as described herein and as understood by one of ordinary skill in the art.

BRIEF DESCRIPTION OF THE DRAWINGS

FIG. 1A shows platelets from 154 healthy human donors were activated by indicated dose of anti-human CD9. Final percentage of aggregation was used as the readout for reactivity. This population was further divided by genetic variation at the codon 131 of FCGR2A gene. Hyper-responders were defined as having higher than 75% final aggregation at 750 ng/mL anti-CD9, while hypo-responders were defined as having lower than 25% aggregation.

FIG. 1B depicts TULA-2 mRNA (UBASH3B) is differentially expressed between 10 top hyper-responders and 10 bottom hypo-responders. All donors were ranked based on the final percentage of aggregation. (Student t-test, P<0.05).

FIG. 1C depicts TULA-2 protein levels as measured by Western blot. The correlation between TULA-2 protein level and TULA-2 mRNA level was determined by Pearson correlation ($R^2$=0.90)

FIG. 1D represents western blot of platelet TULA-2 level in hypo- and hyper-responders.

FIG. 2A shows that at the 48-hour endpoint, cells were lysed and protein were immunoblotted for TULA-2, phosphorylated Syk at tyrosine 525/526 and 323, total Syk, FcγRIIA, and β-actin.

FIG. 2B-C depicts the phosphorylated Syk at tyrosine 525/526 and tyrosine 323 were normalized to total Syk and were plotted as mean±SD against time for the anti-TULA-2 siRNA and scrambled siRNA control groups. (*P<0.05, n=5 for Y323, and n=3 for Y525/526, two-way ANOVA).

FIG. 3A is a Schematic representation of miR-148a-3p (SEQ ID No: 1) and 3'UTR of TULA-2 mRNA interaction. TULA2_148MUT (SEQ ID No: 28) construct was made by mutating 5 out of the 7 nucleotides in the miR-148a binding seed region on TULA-2 3'UTR (SEQ ID No: 26). Mouse TULA-2 mRNA (Ubash3b) (SEQ ID No: 25) varies by two nucleotides outside of the seed region from the human ortholog.

FIG. 3B Luciferase reporter plasmids containing WT 3'UTR of TULA-2 or 148MUT was co-transfected into HCT116-Dicer-KO cells with beta-galactosidase expression vector, and miR-148a-3p mimic or scrambled miRNA control for 24 hours. Bar graph was plotted as normalized. (n=3, *P<0.05)

FIG. 3C shows 60 nM miR-148a-3p or control miRNAs were transfected into HCT-116-Dicer-KO cells or HEL cells by lipofectamine 2000 for 48 hours. TULA-2 protein level was blotted by western blotting.

FIG. 3D depicts the HCT-116-Dicer-KO cells as transfected with 60 nM miR-148a-3p mimic, scrambled miRNA control, anti-miR-148a-3p LNA, or scrambled LNA control by lipofectamine 2000. RNA was isolated 48 hour after transfection and TULA-2 mRNA expression was determined by quantitative RT-PCR (For miRNA overexpression, n=3, *P<0.05. for LNA transfection, n=4, *P<0.05).

FIG. 3E shows the HEL cells as transfected with 100 nM anti-miR-148a or scrambled anti-miR for 48 hours. TULA-2, total Syk, GPVI, and FcγRIIA protein level was detected by immunoblotting.

FIG. 4A depicts the Sequence of the 15-nucleotide anti-miR-148a-3p LNA (SEQ ID No: 21) used to inhibit mmu-miR-148a-3p (SEQ ID No: 1) in vivo, and corresponds to TULE-2 3' UTR (SEQ ID No: 26).

FIG. 4B shows the RNA expression analysis of bone marrow from B6.IIA mouse treated with anti-miR-148a LNA or scrambled LNA control by quantitative RT-PCR. Plots represent four anti-miR-148a treated mice and four scrambled LNA treated mice. Fold change on the Y-axis is plotted as log 2 value. miRNA expression was normalized to mouse let-7 miRNA, TULA-2, FcγRIIA, and GPVI mRNA was normalized to mouse β-actin. miR-148a was significantly decreased by LNA while TULA-2 mRNA expression was upregulated significantly (n=4, *P<0.05 for TULA-2, **P<0.005 for miR-148a).

FIG. 4C illustrates the P-Syk Y519/520, TULA-2 and mouse β-actin protein expression in murine platelet lysates were detected by immunoblotting (representative of three experiments). Mice were treated with control or anti-miR-148a.

FIG. 4D-H Washed anti-miR-148a or control treated platelets as incubated with JON/A alone or indicated concentration of agonists for 10 minutes followed by measurement of JON/A binding (integrin activation) by flow cytometry. All traces are representative of 3 or more independent experiments. Varying concentration of agonists include: (DI) 2 μg/mL IV.3+8 μg/mL GAM. (DII) 2.5 μg/mL CRP. (DIII) 6.25 μg/mL CRP. (DIV) JON/A only or JON/A plus 0.1 U/mL thrombin. (DV) Quantification of mean fluorescent intensity (MFI) fold change (student t test, n=5). Mean fluorescent intensity (MFI) of JON/A-PE and agonists were normalized to background signal of platelets with JON/A-PE alone.

FIG. 6A illustrates a comparison of gross pathologic changes in mouse lungs and spleens between two experimental groups showing pulmonary thrombosis/hemorrhage, and splenic infarction. The control revealing significant damage due to thrombosis in both the lung and spleen, while the anti-miR treated show no gross changes.

FIG. 6B shows the percentage of mice with pathologic changes (n=6 for each group).

FIG. 6C is a microscopic examination of the mouse lungs after induction of thrombosis by anti-CD9 antibody treatment.

FIG. 6D is the Quantification of total clotted vessels from lung histology. Images were captured with Carl Zeiss Axio Observer Z1 microscope and Leica Microsystems DFC 420 camera. Vessel count was conducted under light microscopy. Numbers of clotted vessels was recorded per 200× field. Three separate slides from each treatment group were analyzed. (P<0.01, n=12)

FIG. 14 depicts a luciferase assay for miR-25 and miR-148a.

FIG. 15 depicts a further assay for miR-25 and miR-148a.

FIG. 17 depicts a set of complete miRNA sequences from 5' to 3' and their corresponding anti-miR sequences 5' to 3'. Further depicted are preferred anti-miR sequences corresponding to miR-148a having between 10 and 15 mer. Specifically preferred sequences are depicted and identified as SEQ ID Nos: 19-24. Further anti-miR include the 15 mer sequences of SEQ ID No:29-34, wherein 10 mer are used and additionally one to five of the underlined mer can be included, so as to create a sequence of 10, 11, 12, 13, 14, or 15 nucleotides in length.

DETAILED DESCRIPTION OF THE PREFERRED EMBODIMENTS

Figure 1A:
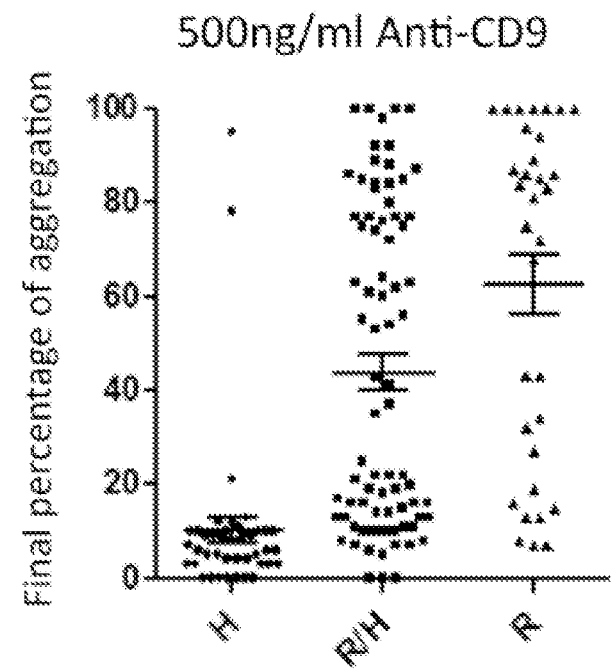
FIGS. 1A-D shows how hyper-responders to FcγRIIA-mediated platelet activation have reduced TULA-2 expression compared to hypo-responders.

The word "about" means within 10% of a stated number.

Blood platelet activation is subject to natural negative regulators. The embodiments disclosed herein increase the level of the natural negative regulators by inhibiting the microRNAs (miR) that control their expression. Antagonism of microRNAs can result in increases in the level of the microRNA targets. Indeed, the preferred embodiments utilize an anti-miR approach that provides an antagonism of a microRNA to increase the level of a protein for the treatment and prevention of thrombosis. This strategy provides a new approach for treatment of thrombosis, wherein conventional pharmacology relies almost exclusively on inhibitors of activators. There is no clinical rationale to inhibit a negative regulator in disorders of unwanted activation, and there are no reports of such an approach for thrombosis in general, or for platelet activation.

Disclosed anti-miRs, including anti-miR 148a-3p, which has been developed for its targeting of the negative regulator T-cell ubiquitin ligand-2, TULA-2. The in vitro and in vivo experimental results demonstrate that (1) mir-148a-3p regulates TULA-2 levels in platelets by direct action on TULA-2 mRNA, (2) anti-miR to miR 148a-3p specifically reduces miR 148a-3p and, at the same time, increases the level of TULA-2 mRNA and TULA-2 protein, and (3) anti-miR to miR 148a-3p specifically prevents thrombosis in vivo in a mouse model of immune-mediated thrombocytopenia and thrombosis with no evident untoward side effects.

MicroRNAs (miRNAs) have been found to inhibit protein expression by inhibiting translation or targeting mRNAs for degradation. Anti-miRNAs, like Locked Nucleic Acids (LNAs), are emerging tools for delivering small, stable RNAs in vitro and in vivo.[24] LNAs are modified nucleic acids containing one or more of the 2'-O, 4'-C-methylene-beta-D-ribofuranosyl nucleosides. LNAs are physiologically stable, resistant to nucleases, have low cytotoxicity, and have robust antisense efficacy and specificity in vivo.[25] In cardiovascular diseases, microRNA inhibition has been used to regulate atherosclerosis, cardiac function and vascular biology in animal models.[26-30] Bhagat et al. showed that anti-miR-21 treatment in mice elevated SMAD7 expression and stimulated hematopoiesis.[31] Garchow et al. identified anti-miR21 effects in a mouse model of systemic lupus erythematosus.[32] Janssen et al. used anti-miR-122 (Miravirsen) to treat human chronic hepatitis C virus infection in phase 2a clinical trial.[33]

However, the effect of in vivo inhibition of miRNAs on platelet reactivity has not been previously reported. In a preferred embodiment, miR-148a-3p and TULA-2 are identified as two mediators of the FcγRIIA pathway. Inhibition of miR-148a increased TULA-2 expression and protected against thrombocytopenia and thrombus formation.

FcγRIIA-mediated platelet activation is essential in heparin-induced thrombocytopenia (HIT) and other immune-mediated thrombocytopenia and thrombosis disorders. There is considerable inter-individual variation in platelet FcγRIIA activation, the reasons for which remain unclear. Based on patient data, genetic variations between FcγRIIA hyper- and hypo-responders appear to regulate FcγRIIA-mediated platelet reactivity and influence HIT susceptibility. Using unbiased genome-wide expression profiling, it was observed that human hypo-responders to FcγRIIA activation showed higher platelet T-cell ubiquitin ligand-2 (TULA-2) mRNA expression than hyper-responders. siRNA-mediated knockdown of TULA-2 resulted in hyper-phosphorylation of spleen tyrosine kinase (Syk) following FcγRIIA activation in HEL cells. Significantly, miR-148a-3p targeted and inhibited both human and mouse TULA-2 mRNA.

This provides for a mechanism to treat patients who are suffering from thrombosis activated diseases, or to prevent the occurrence of these diseases by modification of these pathways. For example, in a cautionary tale, a 54 year old patient was hospitalized with unstable angina and received heparin treatment. On the fourth day, the patient experienced sudden onset of sever foot pain and paleness and the patient's platelet count dropped to 50,000/mm3. Just five hours later, the patient developed dyspnea and chest pain and died shortly thereafter, despite aggressive treatment of her symptoms. She was suffering from HIT, which resulted in the formation of thrombosis, which led to her ultimate demise. The compositions, methods, and kits described herein provide mechanisms to treat HIT and other thrombosis diseases.

Unfortunately, there is a lack of data about why some patients suffer from HIT after heparin treatment and who others do not. Indeed, it appears that genetic variations between platelet FcγRIIA is responsible for hyper and hypo responders to heparin treatment. Of course, similar issues are present for patients who suffer deep vein thrombosis or pulmonary embolisms. While certain risk factors may contribute to these medical emergencies, genetic variation may also play a large role in who is most susceptible to such issues. The ability to treat patients with a composition that would target the platelet activation to reduce or eliminate the risk of the thrombosis would be a major development for treatment of these patients.

Many recent studies[11,14,15] have focused on the molecular mechanism by which FcγRIIA promotes platelet activation, however, less is known about negative regulators of the signaling pathway. TULA-2, a protein tyrosine phosphatase identified as a negative effector of FcγRIIA as described herein, is encoded by the UBASH3B (Ubiquitin associated and SH3 domain-containing protein B) gene. It belongs to the TULA family of proteins, with TULA-2 as the sole family member detectable in platelets.[16] TULA-2 functions as a tyrosine phosphatase, and, a deficiency of TULA-2 results in the hyperphosphorylation of Syk homolog Zeta-chain-associated protein kinase 70 (ZAP70) in T-cells.[17-19] TULA-2 also associates with Syk and negatively regulates murine platelet activation via GPVI/FcRγ, another ITAM-containing receptor complex.[20] GPVI/FcRγ is the primary receptor for platelet-collagen interaction.[21]

Inhibition of miR-148a in FcγRIIA transgenic mice up-regulated the TULA-2 level and reduced FcγRIIA- and GPVI-mediated platelet $α_{IIb}β_3$ activation and calcium mobilization. Anti-miR-148a also reduced thrombus formation following intravascular platelet activation via FcγRIIA. Accordingly, TULA-2 is a target of miR-148a-3p and TULA-2 serves as a negative regulator of FcγRIIA-mediated platelet activation. Therefore, by targeting TULA-2 in vivo, it is possible to decrease or eliminate thrombosis formation by decreasing platelet activation in the patient. Accordingly, by providing an anti-miR that corresponds to a miR that is a target of TULA-2, modification of thrombosis formation and platelet activation can be achieved.

Three concentrations of an anti-CD9 antibody ($mIgG_1$ isotype) were used in a prior PRAX-1 study as a model of FcγRIIA-mediated platelet activation relevant to HIT.[13] Platelet FcγRIIA surface protein expression level and the H/R131 SNV genotype (r51801274) were determined for each donor, since these variations have previously been reported as contributing to variation in platelet activation via FcγRIIA.[10,36-38] A $mIgG_1$ agonist was used specifically to replicate the known dependence on the RH polymorphism. R/R131 homozygotes were highly responsive to the $mIgG_1$ anti-CD9, and H/H homozygotes were weakly responsive (FIG. 1), as expected.[36]

It is particularly striking then to see the wide variation in reactivity among donors identical for the RH heterozygous genotype. These individuals all had a platelet surface FcγRIIA expression level within 2 standard deviations of the mean for the PRAX-1 cohort. The FcγRIIA level accounts for 12% of the observed variance. After controlling for the previously recognized sources of variation in platelet FcγRIIA reactivity, the expression level and the H/R131 genotype, a major, unexplained variation (88%) in reactivity was observed.

Figure 1B:
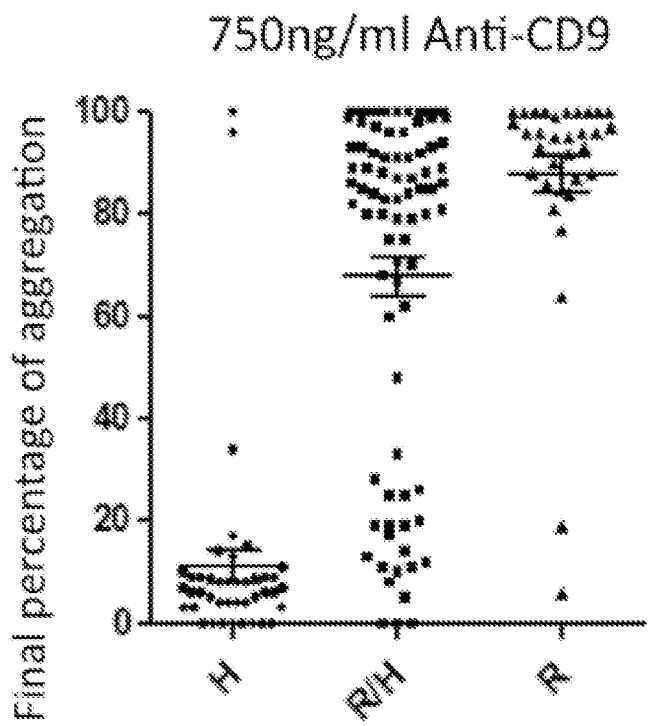
Figure 1C:
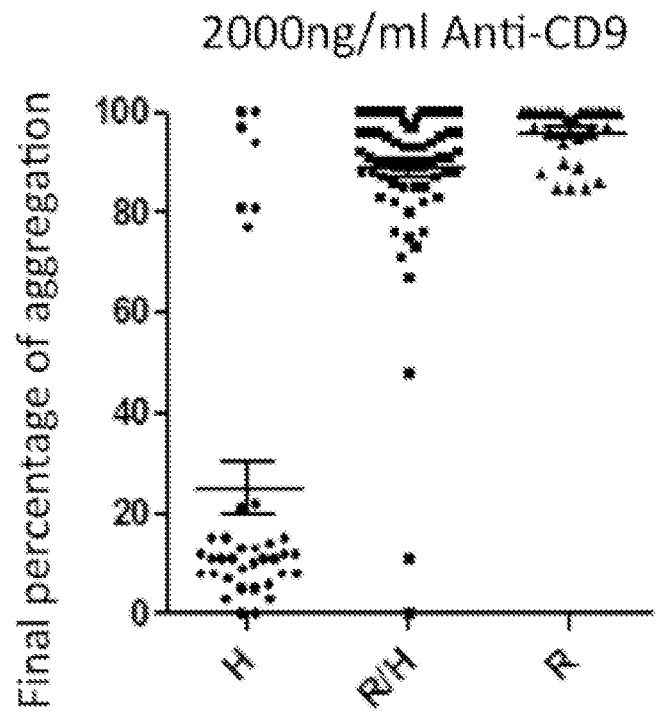
Figure 1D:
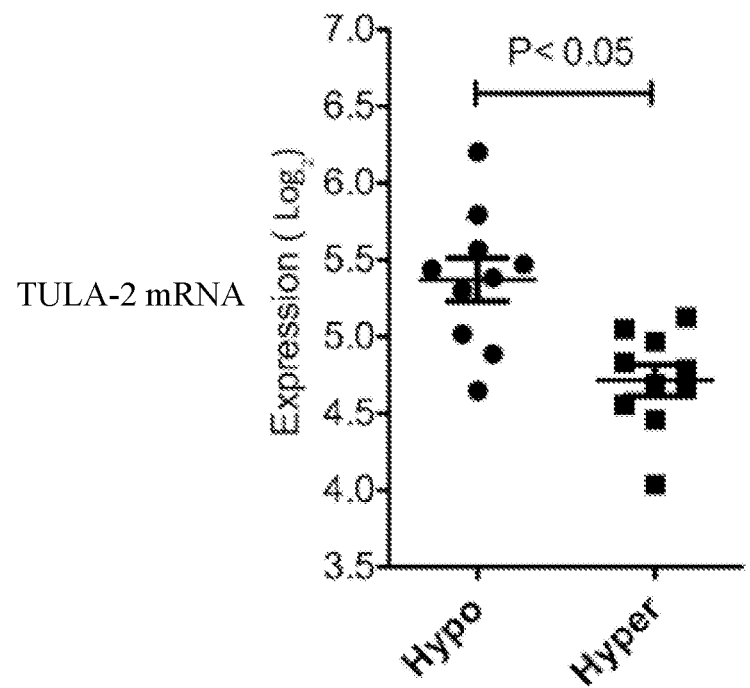
Figure 1E:
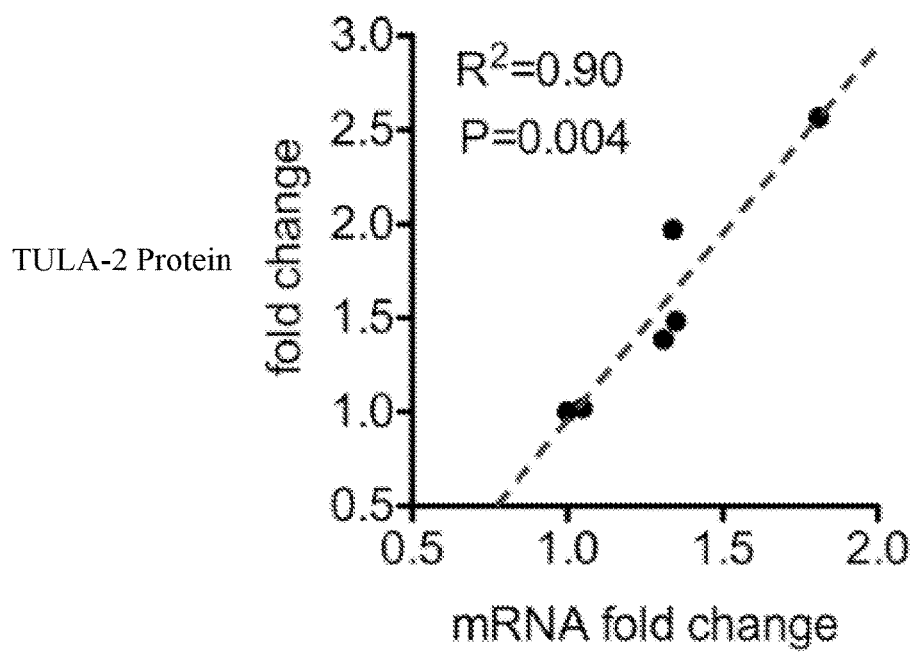
Figure 1F:
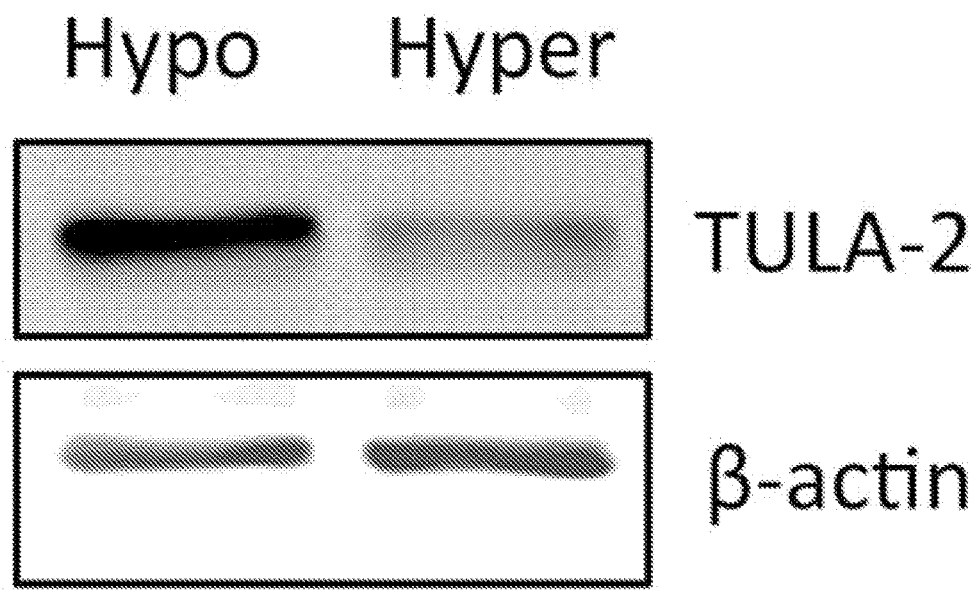

In order to elucidate the molecular basis of the unexplained variation in reactivity, hyper-responders and hypo-responders were defined among the R/H131 heterozygotes as greater than 75% final aggregation and less than 25% final aggregation in response to 750 ng/mL anti-CD9, respectively (FIG. 1A). Gene expression profiling identified 76 differentially expressed (DE) mRNAs between FcγRIIA hyper- and hypo-responders, 54 up and 22 down in hypo-responders. The DE mRNAs were analyzed using Gene Ontology (www.geneontology.org) and KEGG analyses (www.genome.jp/kegg/), and genes that are involved in protein tyrosine phosphorylation and in ubiquitylation processes were enriched in these lists (data not shown), including TULA-2, which was upregulated in hypo-responders. Notably, TULA-2 was not DE with respect to ADP-, PAR1- or PAR4-mediated platelet reactivity (www.plateletomics.com[13]). The top 10 hypo-responders to FcγRIIA activation showed significantly higher TULA-2 platelet mRNA expression than the bottom 10 hyper-responders (FIG. 1B). Furthermore, TULA-2 protein level measured by western blotting correlates well with the mRNA level (FIG. 1C, D).

Biological Validation of the Function of Differentially Expressed TULA-2

Figure 2A:
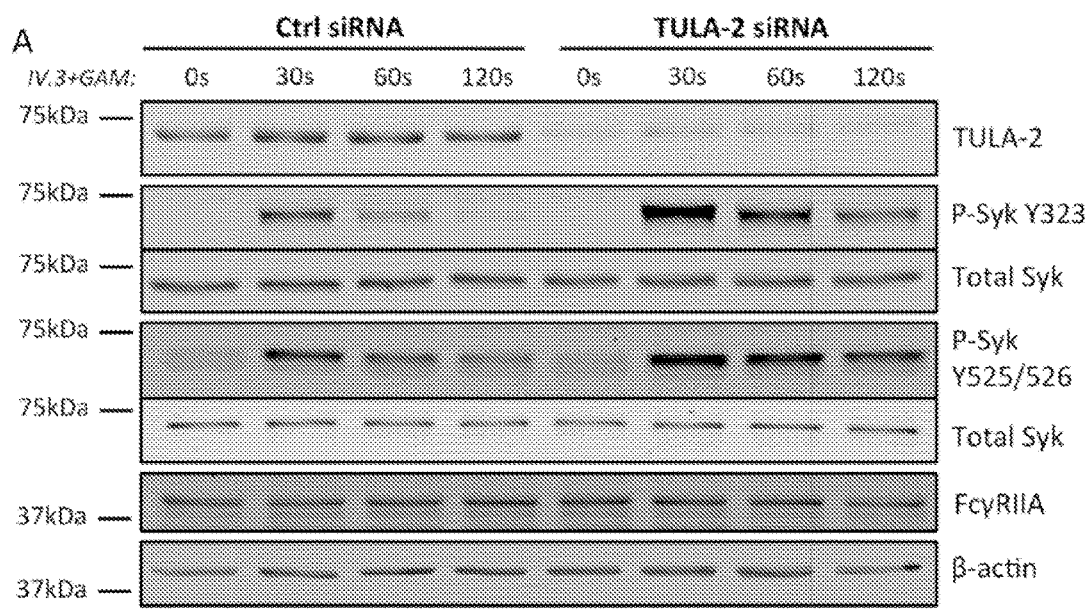
FIGS. 2A-C depicts the TULA-2 dephosphorylates Syk in FcγRIIA pathway.
Figure 2B:
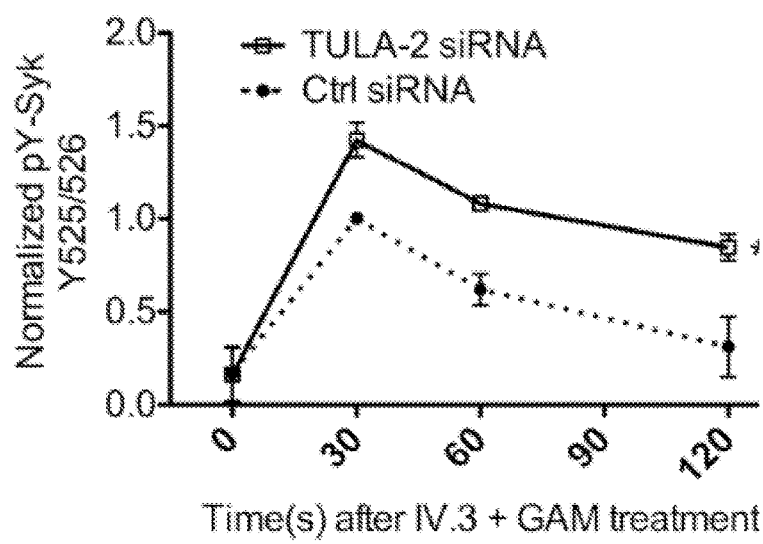
Figure 2C:
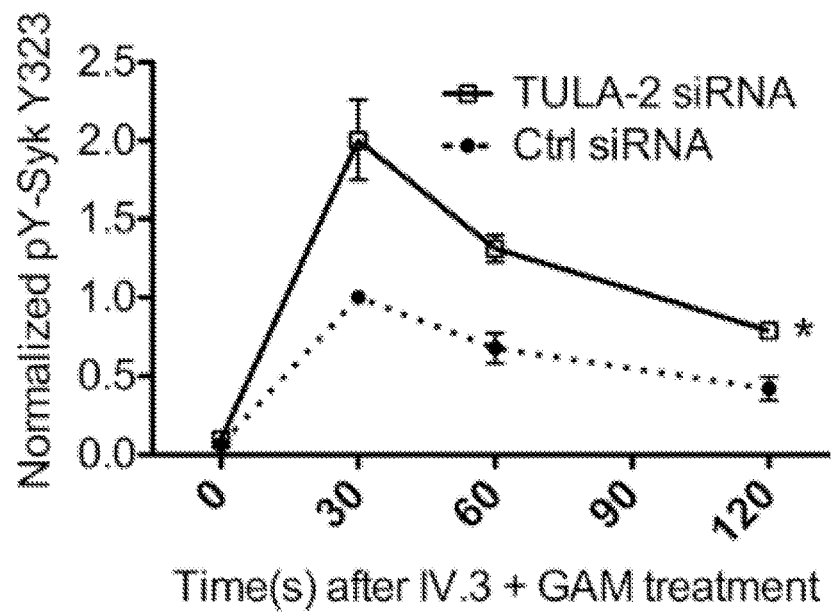

The data identifies that TULA-2 serves as a negative regulator of FcγRIIA signaling by inactivating phospho-Syk. Syk is phosphorylated upon activation at multiple tyrosine residues including Y323, Y352 and Y525/526. TULA-2 knockout mice have been reported to have hyperphosphorylation of Syk at several sites, including Y323 and Y525/526 tyrosine residues.[18,39] Accordingly, the examples looked at Y525/526 and Y323 as the readout for Syk activation in HEL cells for platelet FcγRIIA signaling. Cross-linking FcγRIIA by an anti-FcγRIIA antibody (IV.3) and goat anti-mouse $Fab'_2$ (GAM) induces receptor clustering and activation, which leads to phosphorylation of Syk in HEL cells. In scrambled control siRNA-transfected HEL cells, phosphorylation of Syk at both Y525/526 and Y323 peaked at 30 seconds after receptor cross-linking and slowly declined. In contrast, down-regulation of TULA-2 showed a significantly higher level of phosphorylated Syk (P<0.05, FIG. 2A, B), consistent with TULA-2 dephosphorylating Syk in FcγRIIA signaling.

miR-148a Targets TULA-2 mRNA and Downregulates TULA-2 Protein Expression.

Figure 3A:
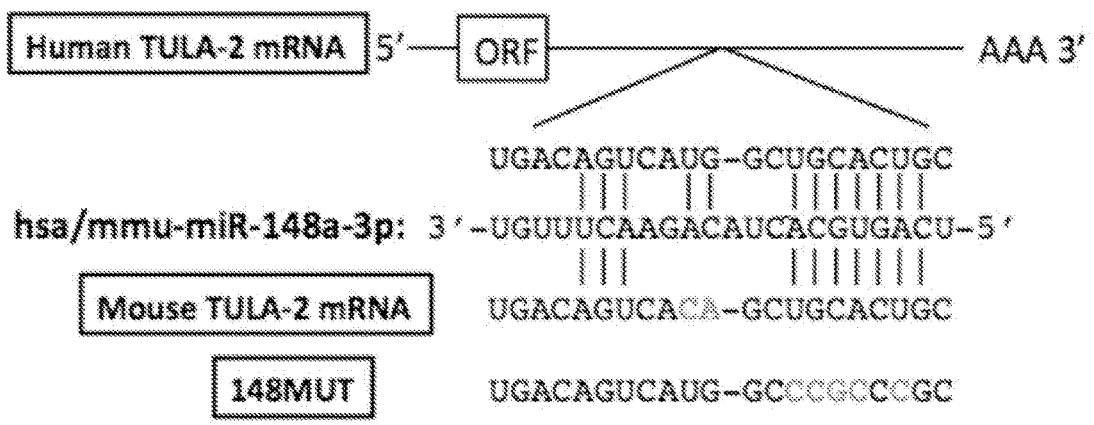
FIGS. 3A-E shows how miR-148a targets 3'UTR of TULA-2 mRNA and downregulate the protein expression.
Figure 3B:
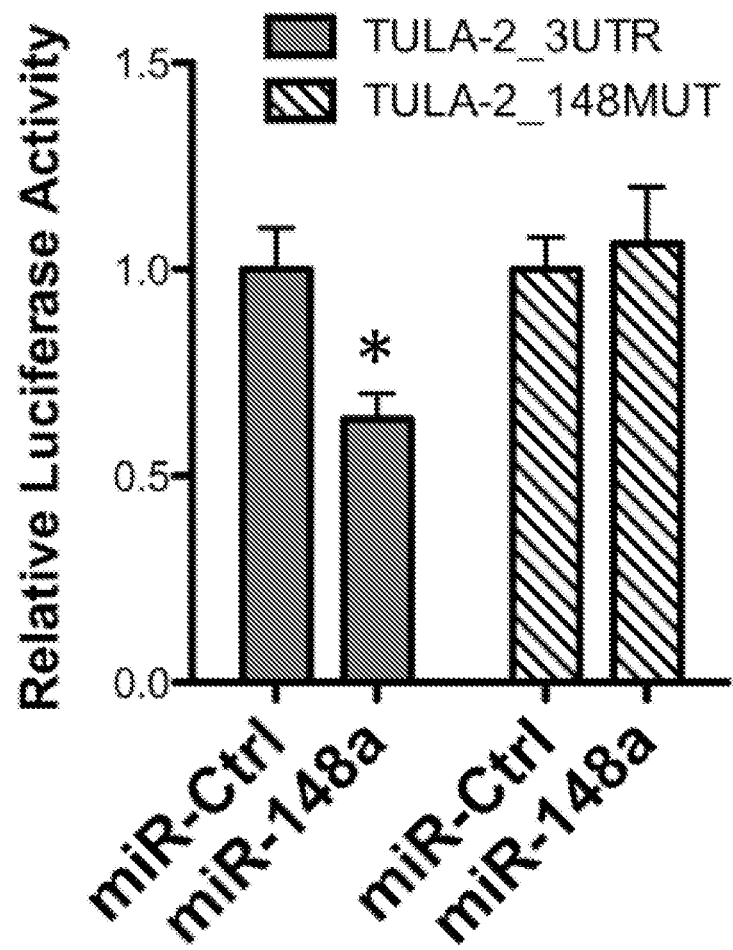

To investigate the mechanism of differential expression of TULA-2, it was important to identify regulators of TULA-2 in platelets that might influence platelet reactivity. TargetScan (www.targetscan.org) and RNA22[40] programs were used to screen for microRNAs predicted to target TULA-2. miR-148a-3p was selected for further study for three reasons: (1) miR-148a-3p was predicted by RNA22 and TargetScan to bind at the seed position 1111-1118 of the TULA-2 3'UTR (FIG. 3A); (2) it is highly expressed in the megakaryocyte-platelet lineage; and, (3) the miR-148a sequence as well as the potential binding site on TULA-2 is conserved between human and mouse. Therefore, while certain studies were performed with human cells additional studies using mouse models were utilized in certain instances.

miR-148a-3p is the predominant form over miR-148a-5p (http://www.mirbase.org/). To investigate whether miR-148a interacts directly with the putative binding site on TULA-2, the luciferase reporter plasmid containing the 3'UTR of TULA-2 (SEQ ID No: 26 was co-transfected along with the miR-148a-3p in HCT cells. A mutant construct (TULA2_148MUT) (SEQ ID No: 28) was created as a control (FIG. 3A). For the luciferase reporter containing WT TULA-2 3'UTR (SEQ ID No: 26), miR-148a-3p (SEQ ID No: 1) overexpression significantly decreased luciferase activity compared with control miRNA mimic. In contrast, miR-148a-3p overexpression failed to downregulate TULA-2_148MUT construct, suggesting that the 7-nucleotide seed match is responsible for miR-148a and TULA-2 interaction (FIG. 3B).

Figure 3C:
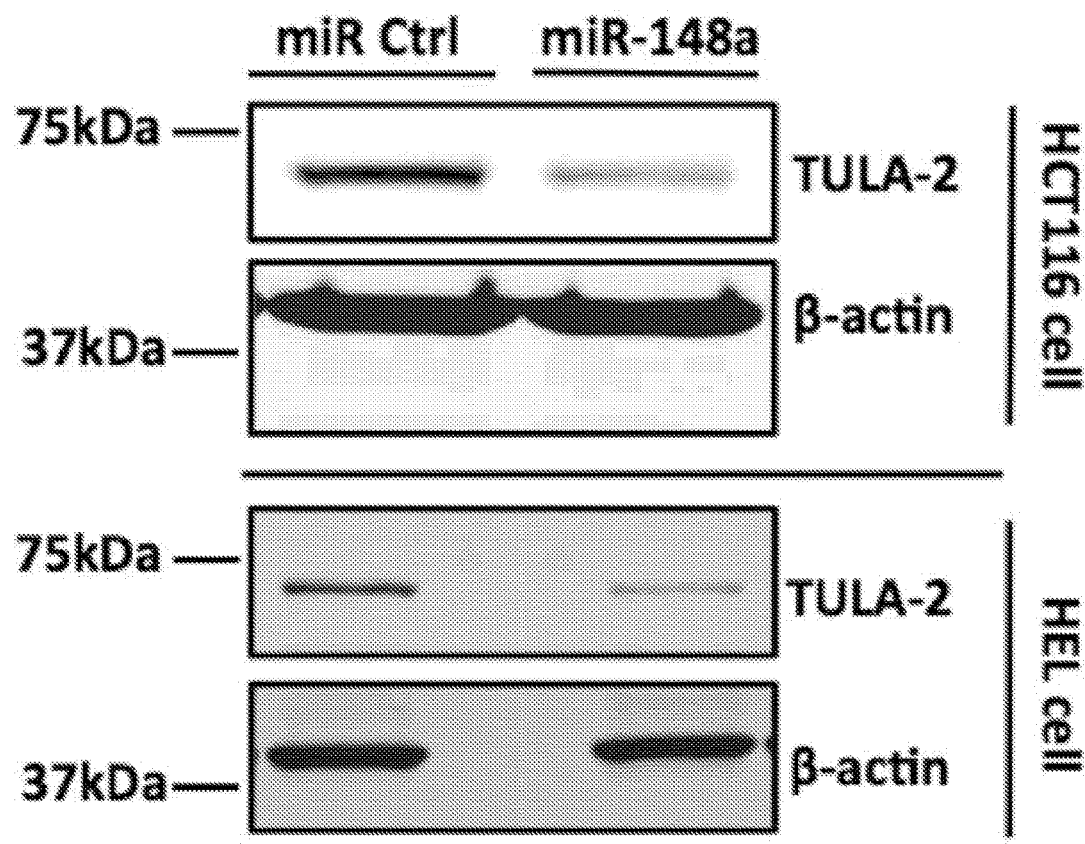
Figure 3D:
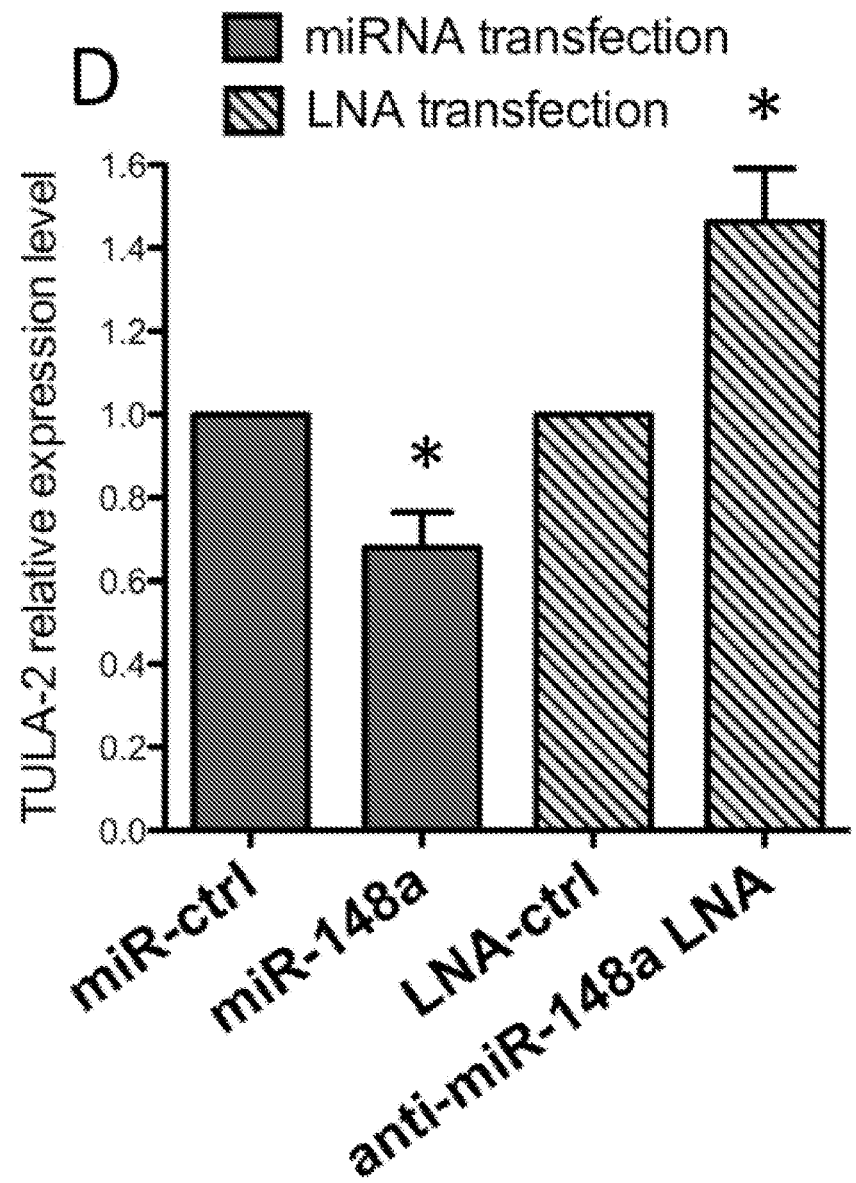

To confirm the match, a further test was run to overexpress miR-148a-3p in HEL cells as well as in HCT cells for 48 hours. Overexpression of miR-148a-3p significantly decreased the TULA-2 mRNA level (FIG. 3D). Consistent with the luciferase assay and the mRNA results, miR-148a-3p overexpression led to decreased TULA-2 protein expression (FIG. 3C).

Downregulation of miR-148a LED to De-Repression of TULA-2 In Vitro.

Figure 3E:
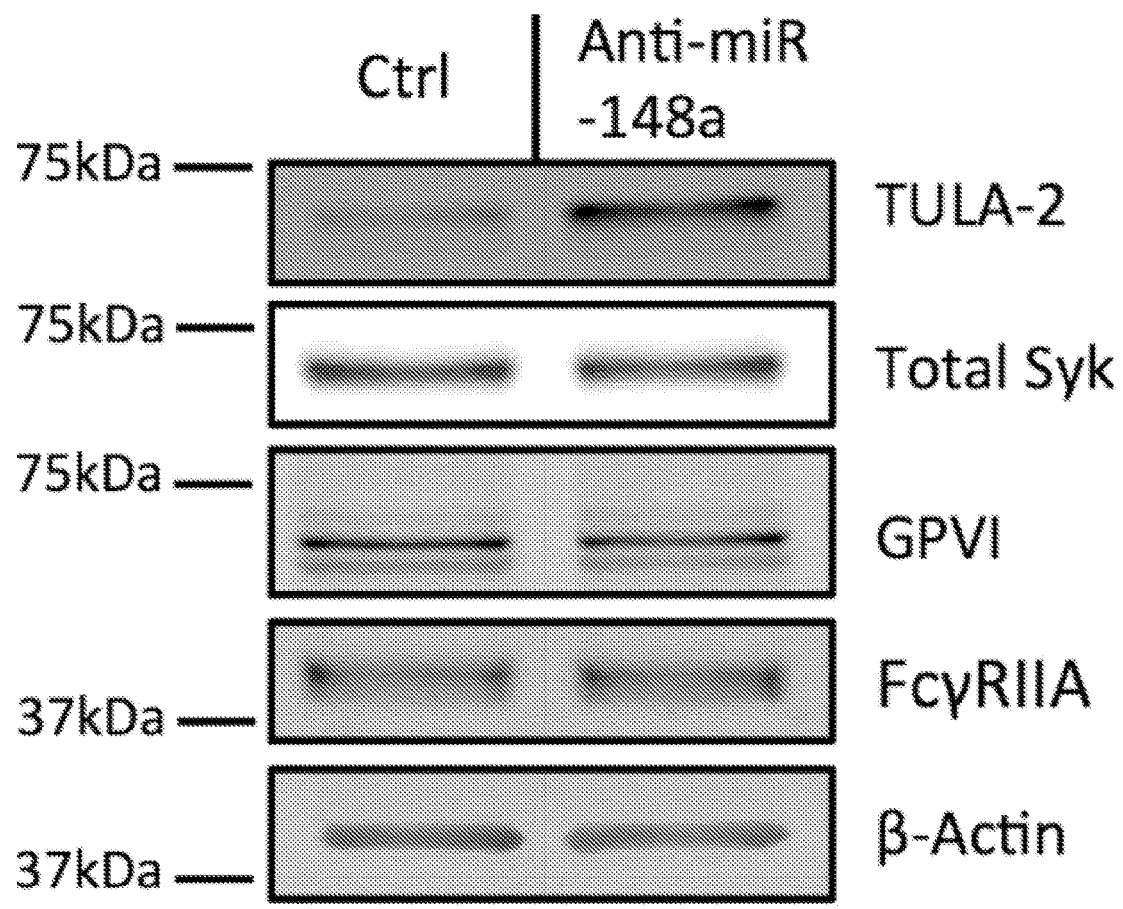

The effect of endogenous miR-148a-3p on TULA-2 mRNA was further tested by overexpressing an anti-miR-148a-3p in HEL cells. Inhibition of endogenous miR-148a-3p led to increased TULA-2 mRNA expression (FIG. 3D). The TULA-2 protein level was also increased by the anti-miR-148a, while Syk, GPVI, and FcγRIIA were unaffected by miR-148a inhibition (FIG. 3E). Together these results identified miR-148a-3p as a regulator of TULA-2.

Anti-miR-148a-3p LNA Represses Endogenous Murine mmu-miR-148a-3p, Up-Regulates Platelet TULA-2, and Leads to Hypo-Phosphorylation of Syk.

Figure 4A:
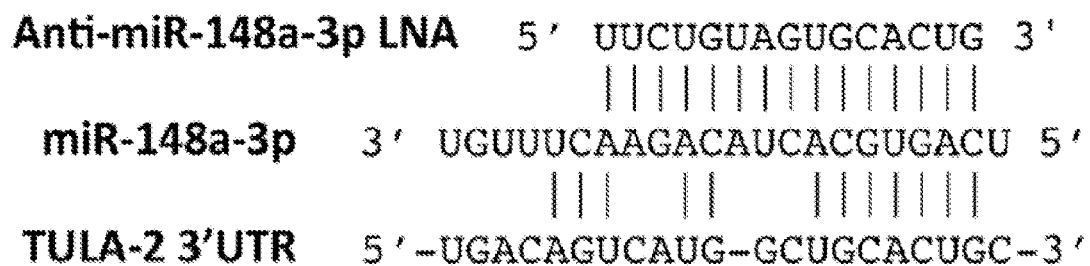
FIG. 4A-D shows that the anti-miR-148a LNA (SEQ ID No: 21) de-represses TULA-2 expression and inhibits ITAM-Syk signaling in vivo.

Based on these experiments, it was hypothesized that the inhibition of miR-148a would increase the TULA-2 protein level and attenuate FcγRIIA-mediated thrombosis in vivo. Mice lack FCGR2A gene encoding the FcγRIIA receptor. A mouse model, transgenic for human FcγRIIA as previously described, was utilized.[4] Murine miR-148a-3p shares the same sequence with its human counterpart and it is expressed in murine platelets and megakaryocytes (data not shown). FcγRIIA transgenic mice were treated with 25 mg/kg anti-miR-148a or scrambled anti-miR control for five times total on alternative days. The treatment used the protocol of Bhagat et al., who used this approach in modulating mouse hematopoietic cell miRNA.[31] The sequence of the chosen 15-nucleotide anti-miR (SEQ ID NO: 24) is complementary to mmu/hsa-miR-148a-3p sequence (SEQ ID No: 1) (FIG. 4A). Also depicted in FIG. 4A is SEQ ID No: 26), which corresponds to the TULA-2 3' UTR region.

Figure 4B:
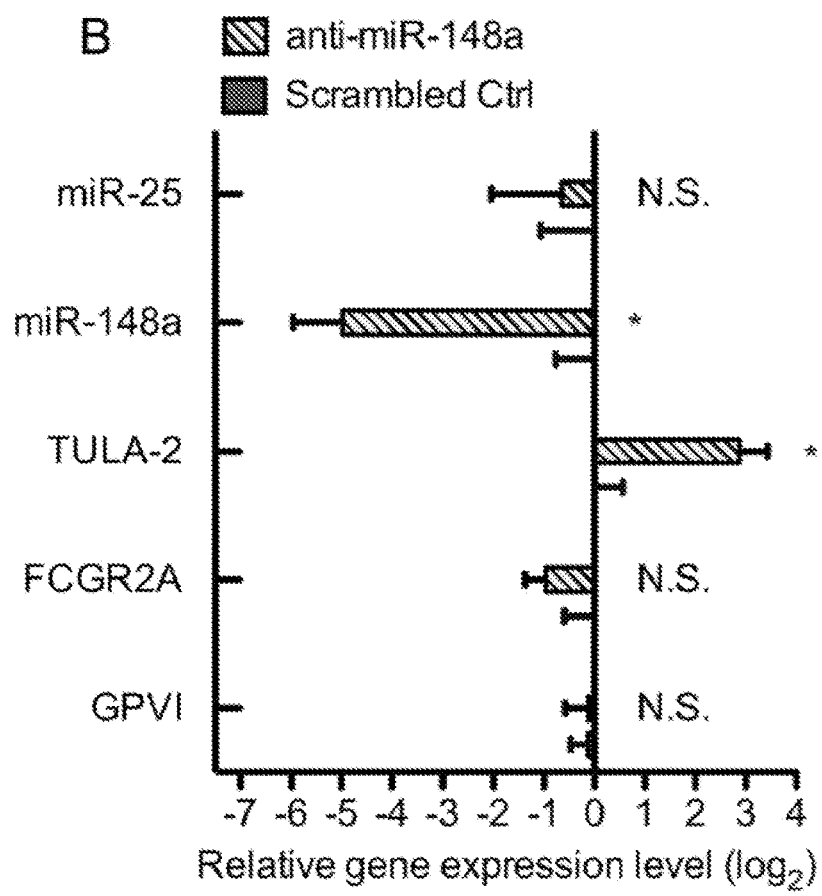
Figure 4C:
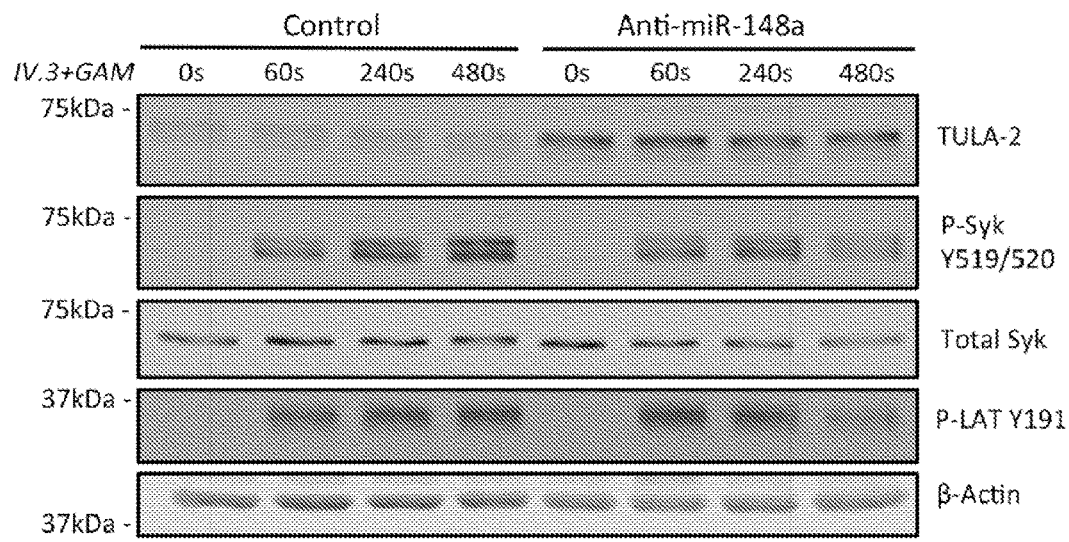
Figure 4D:
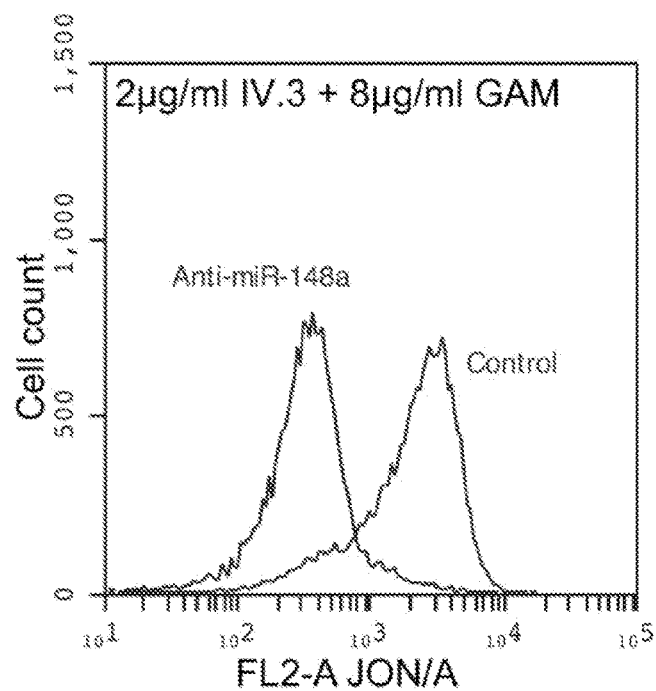
Figure 4E:
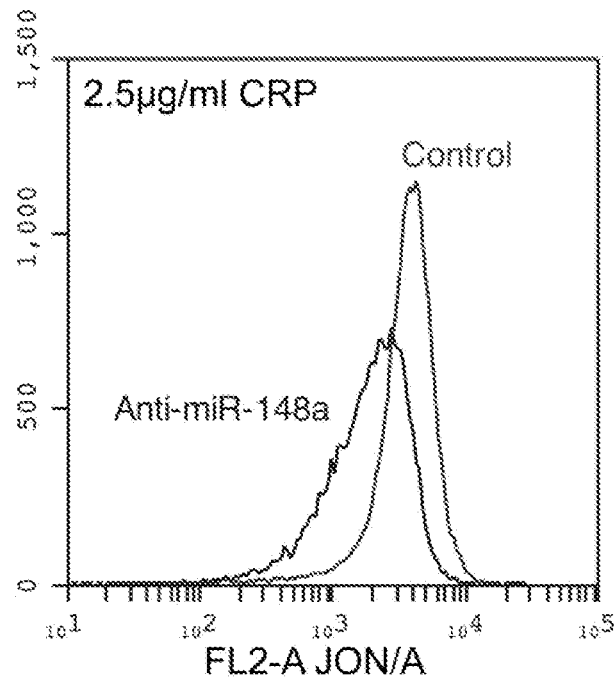
Figure 4F:
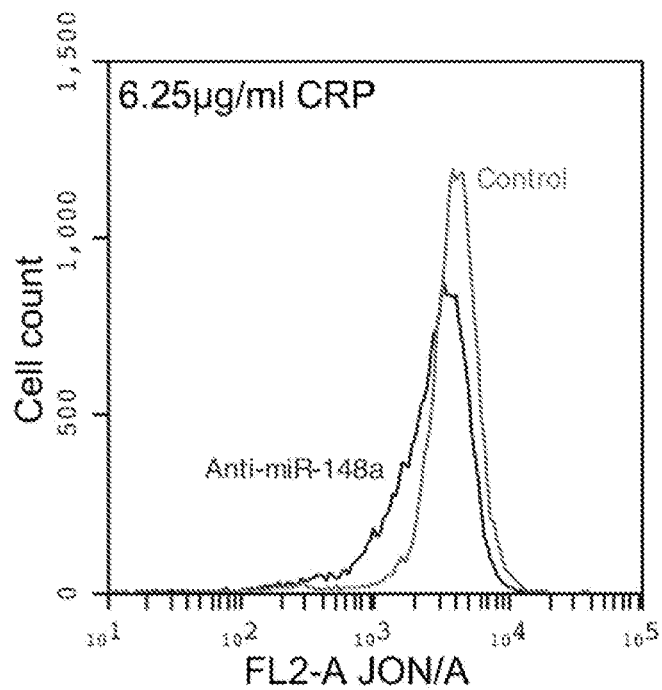
Figure 4G:
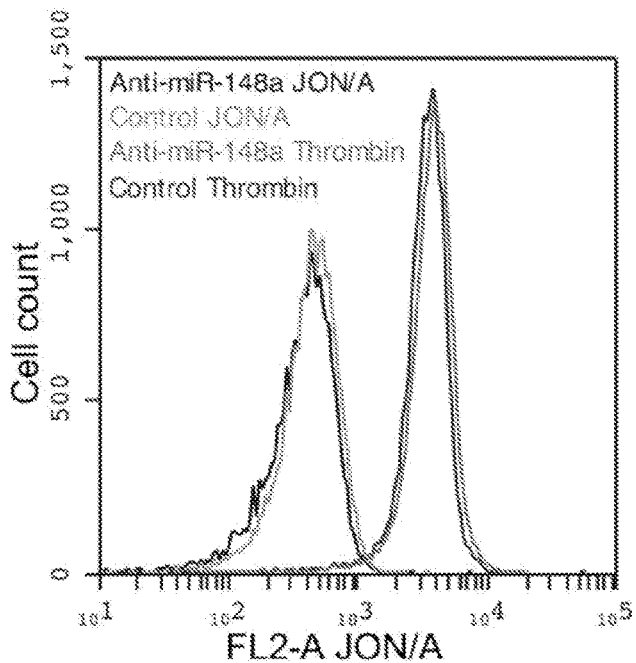
Figure 4H:
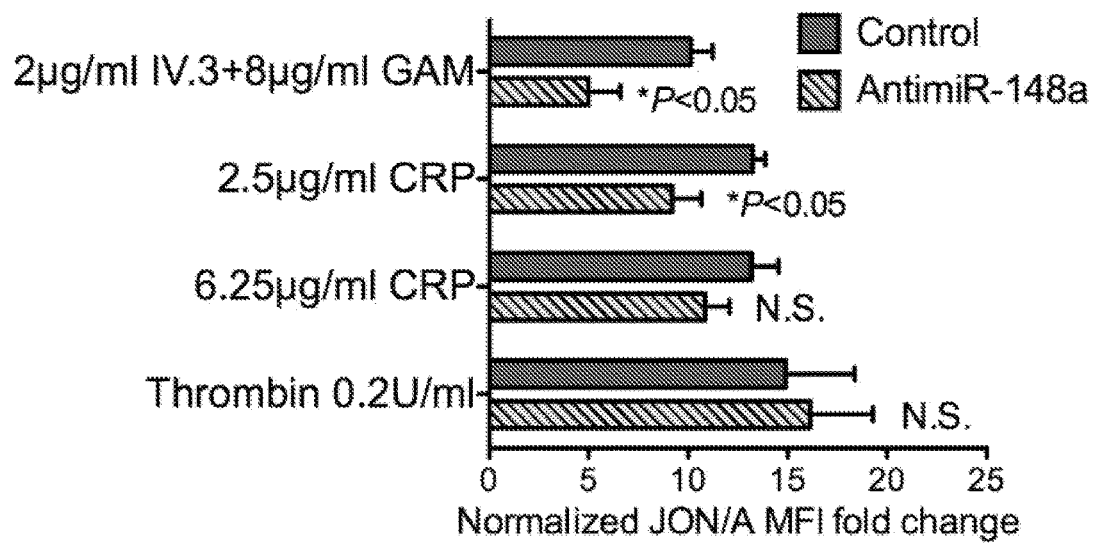
Figure 9A:
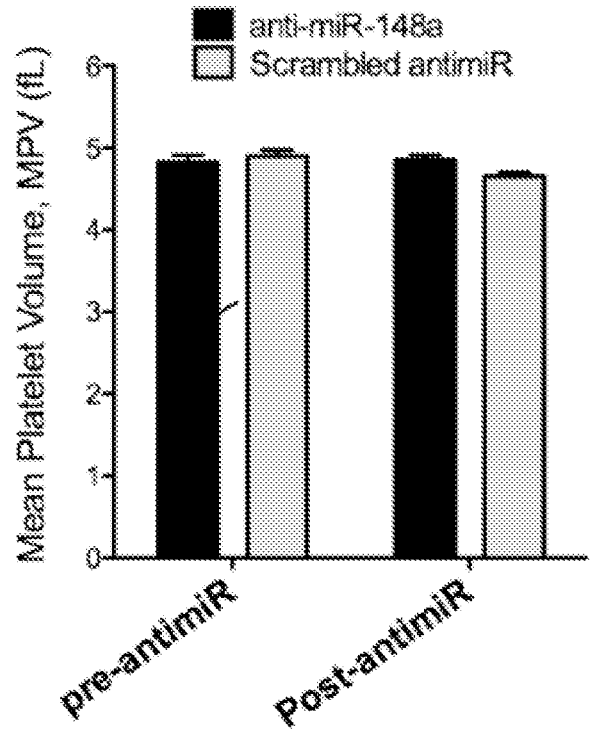
FIG. 9A illustrates changes in mean platelet volume (MPV) before and after anti-miR treatment.
Figure 9B:
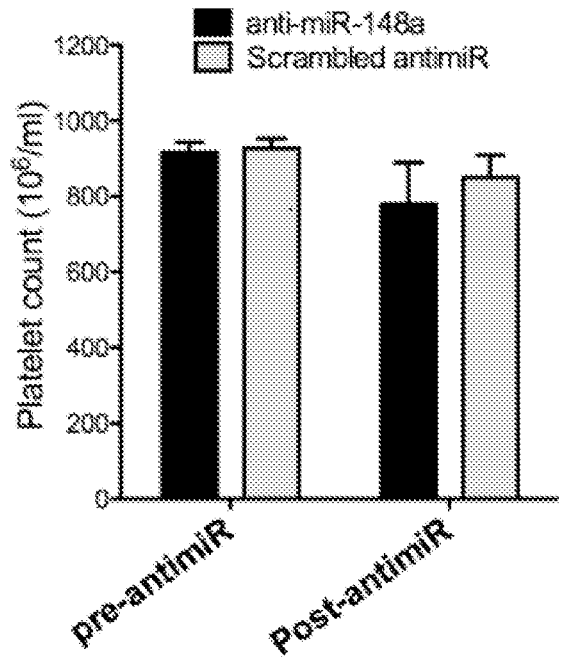
FIG. 9B illustrates changes in platelet count before and after anti-miR treatment.
Figure 9C:
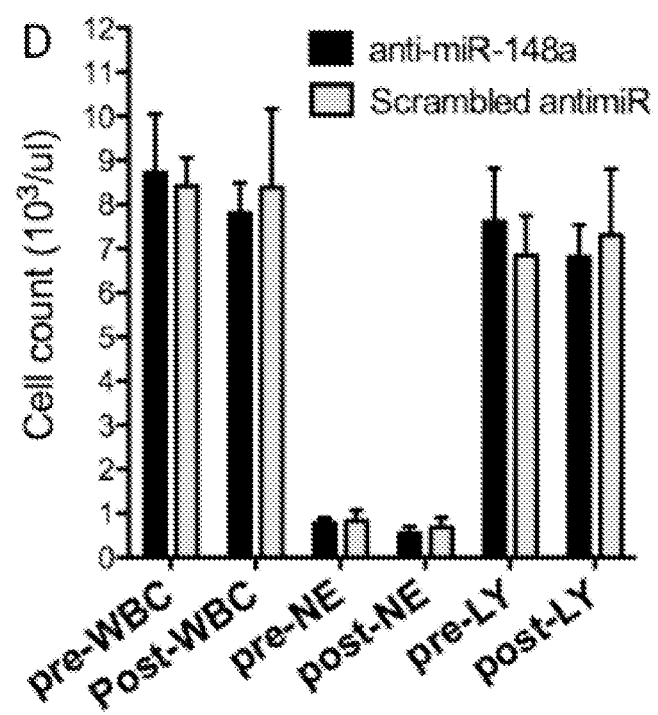
FIG. 9C illustrates the WBC counts pre and post anti-miR treatment.

No mice showed any observable changes in behavior or gross pathologic abnormalities during the 14-day period of administration of either anti-miR. Platelet count, mean platelet volume, or other blood cell counts were not changed by LNA treatment (FIG. 9A-C). Compared to the scrambled control group, anti-miR148a-treated mice showed a significant drop (97%) in miR-148a expression in mouse bone marrow (FIG. 4B). As a negative control, miR-25 level remained unaffected (data not shown). TULA-2 mRNA level showed the opposite trend: anti-miR148a treatment significantly increased TULA-2 expression level (FIG. 4B). On the other hand, FCGR2A as well as GPVI mRNA, that do not contain potential miR-148a binding sites, were not changed by anti-miR (FIG. 4B). In platelets, TULA-2 protein level was elevated by anti-miR-148a to more than threefold, and phosphorylation of Syk after FcγRIIA activation was subsequently reduced by 50% at 480 s under non-stirring condition (FIG. 4C, FIG. 9B).

Inhibition of Endogenous Murine mmu-miR-148a-3p Diminished Platelet Reactivity Via FcγRIIA and GPVI.

The effect of the anti-miR was tested on two Syk-mediated platelet functions: integrin activation and calcium mobilization. Murine platelets from anti-miR-148a treated mice or control mice were washed and activated by different doses of IV.3+GAM or collagen-related peptide (CRP). Integrin $\alpha_{IIb}\beta_3$ activation is crucial in platelet-fibrinogen and vWF binding, hemostasis and thrombosis.[41-43] FcγRIIA activation by 2 μg/mL IV.3 and 8 μg/mL GAM in anti-miR-148a treated murine platelets showed 50% reduction in integrin activation compared to control group. CRP-induced integrin activation was also diminished at a concentration of 2.5 μg/mL by anti-miR-148a treatment (FIG. 4D-H). As a non-ITAM-agonist control, thrombin did not induce differential integrin activation (FIG. 5D).

Figure 5A:
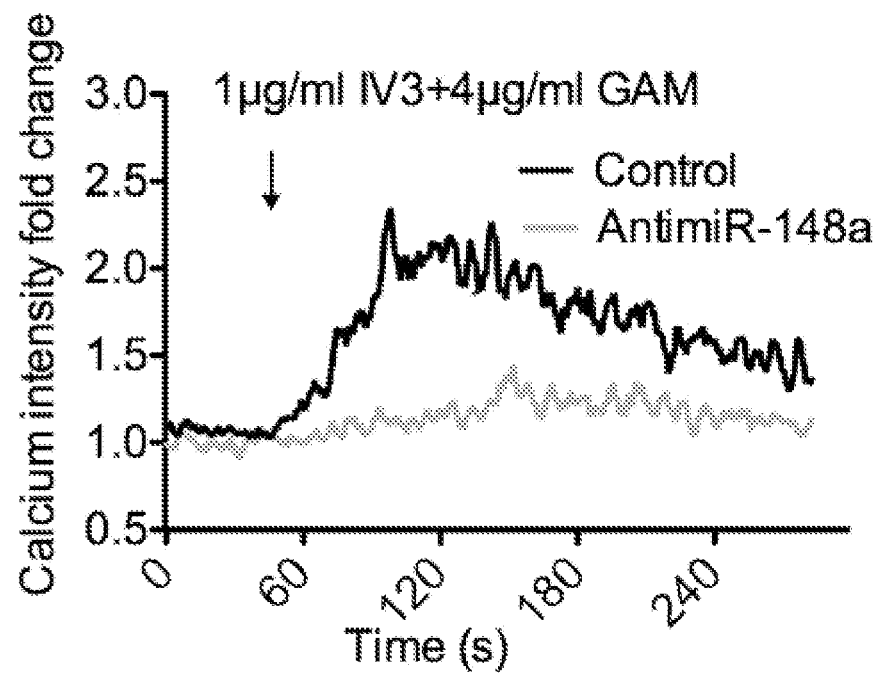
FIGS. 5A-I depict the in vivo miR-148a inhibition diminished calcium mobilization via GPVI and FcγRIIA stimulation. 1×106 platelets from anti-miR-148a or control treated mice were labelled with Fluo-4-AM. Baseline intracellular calcium was assessed for 60 seconds and indicated doses of agonists were added to the platelets: (A, B) 1 μg/mL IV.3+4 μg/mL GAM and 2 μg/mL IV.3+8 μg/mL GAM were added respectively at indicated time. (C) Quantification of peak calcium fold change (n=3). (D) Quantification of area under the curve (AUC) for calcium mobilization curve (n=3). AUC was calculated in Prism software. (E, F, G) 2.5 μg/mL CRP, 6.25 μg/mL CRP, and 12.5 μg/mL CRP were used to induce calcium influx respectively. (H, I) Quantification of peak calcium fold change and AUC was performed as discussed above (n=3).
Figure 5B:
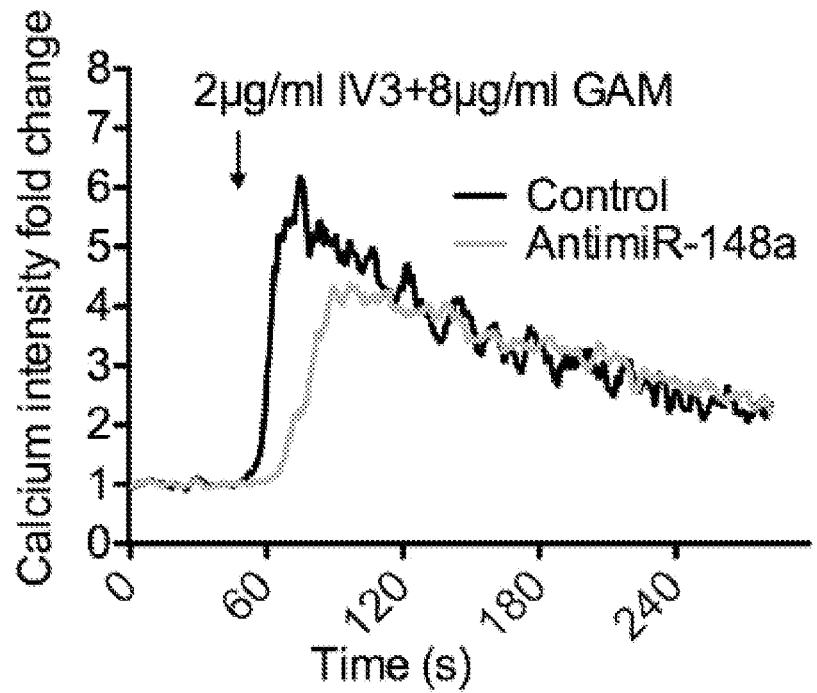
Figure 5C:
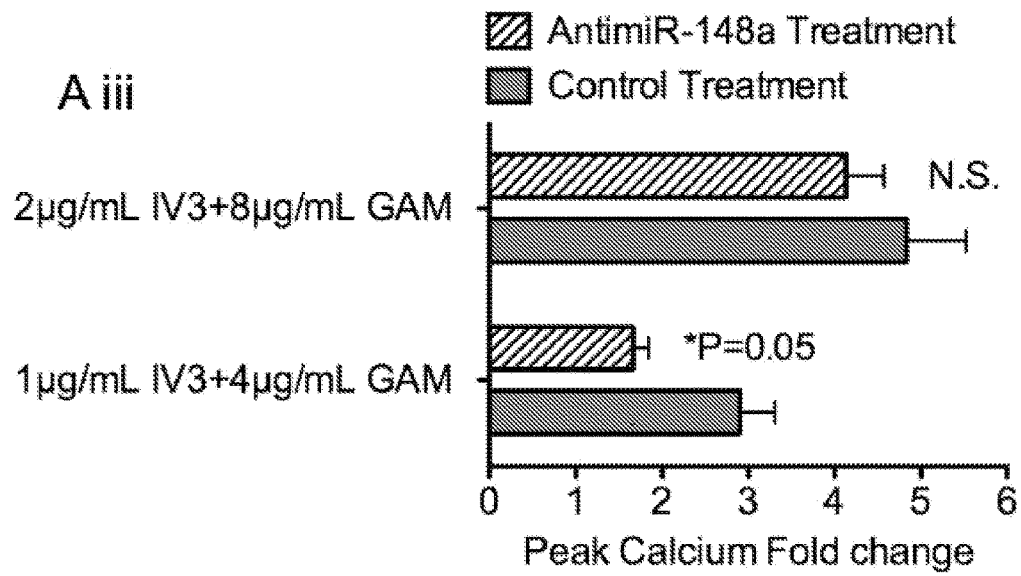
Figure 5D:
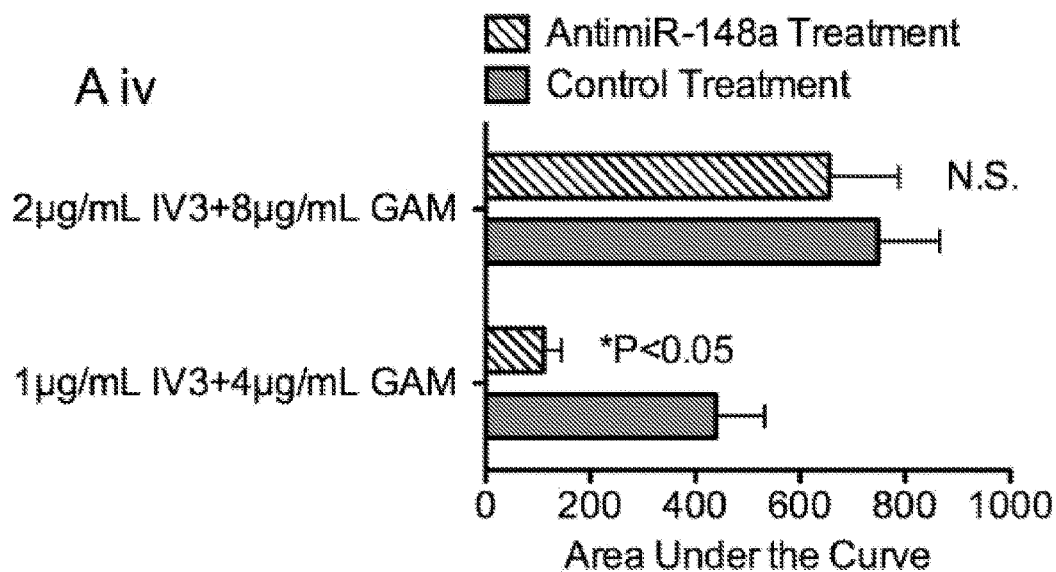
Figure 5E:
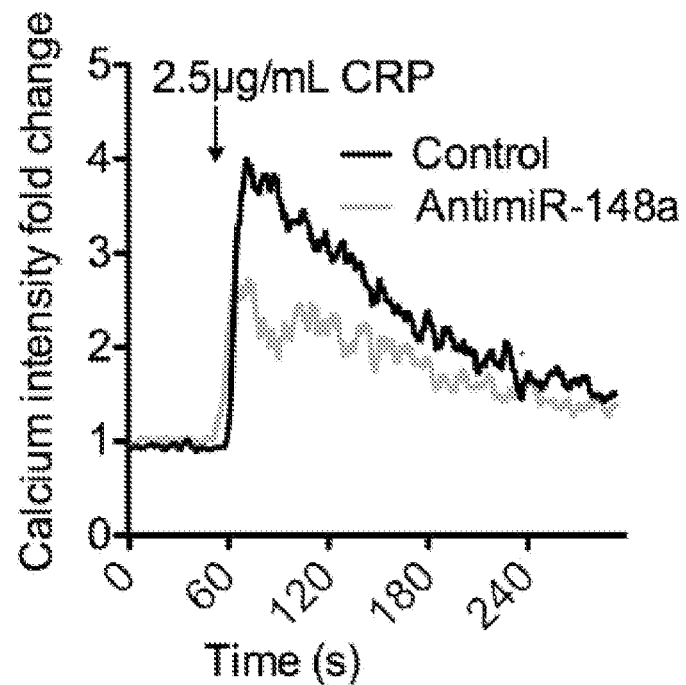
Figure 5F:
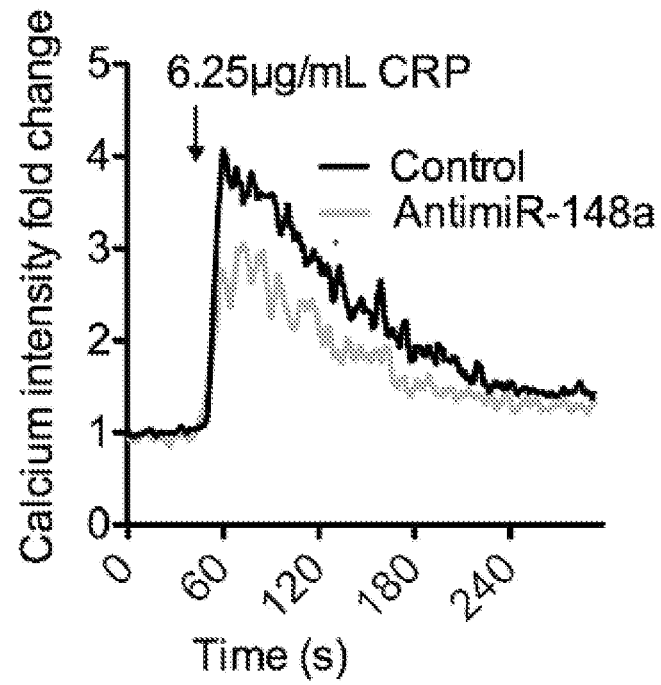
Figure 5G:
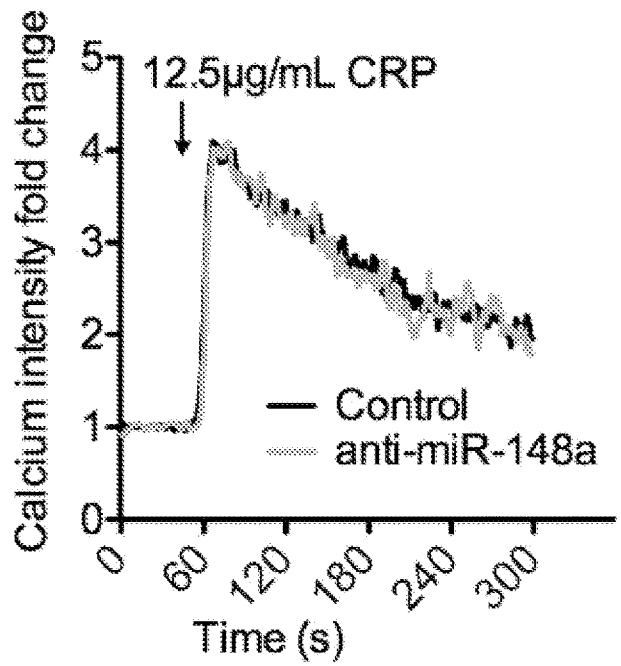
Figure 5H:
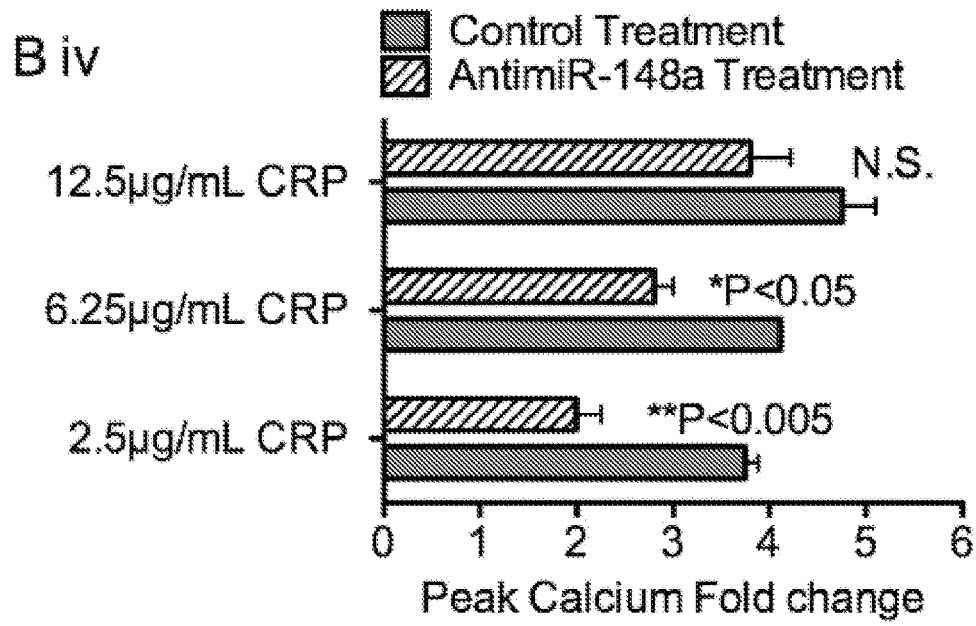
Figure 5I:
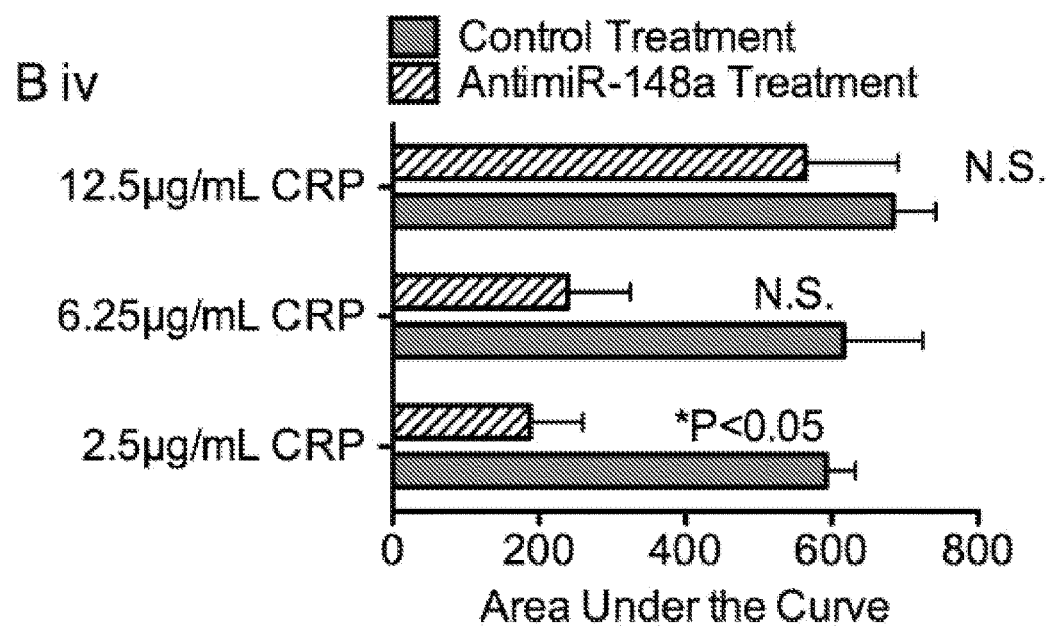

Increased cytoplasmic calcium plays a critical role in platelet reactivity.[44] In miR-148a knockdown platelets, 70% decreased calcium influx (area under the curve) was observed when induced by 2.5 μg/mL CRP (FIG. 5B). 1 μg/mL IV.3 and 4 μg/mL GAM treatment also showed impaired calcium influx in the anti-miR-148a treated platelets (FIG. 5A). Taken together, miR-148a inhibition attenuated FcγRIIA- and GPVI-mediated platelet reactivity.

Inhibition of miR-148a in Vivo by an Anti-miR Protects FcγRIIA-Mediated Thrombosis.

Figure 8:
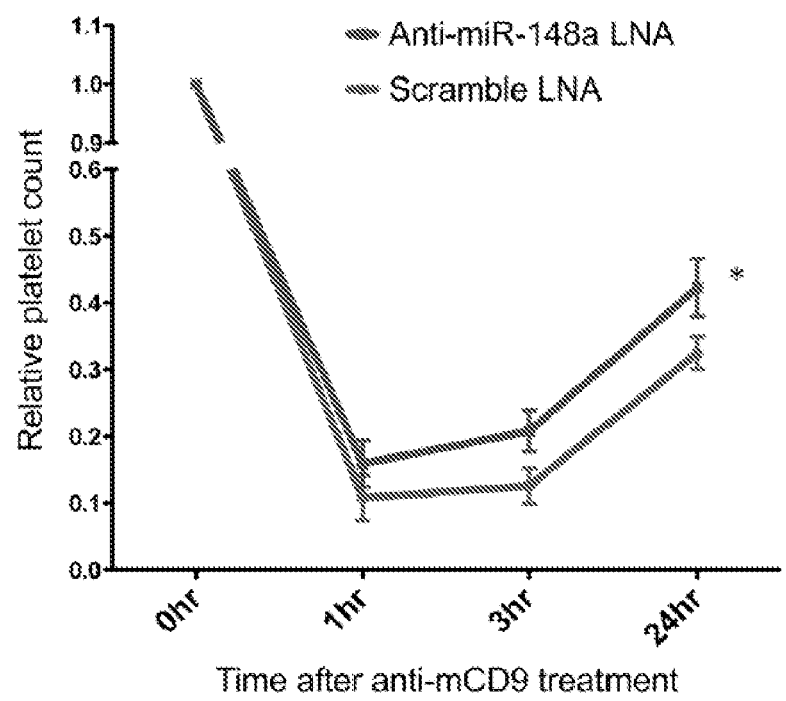
FIG. 8 shows the relative platelet count of six anti-miR-148a treated mice and six scrambled LNA treated mice was plotted against time after anti-CD9 treatment to induce HIT-like symptoms. Mice treated with anti-miR-148a experienced less platelet drop than the control group at 1 hour, 3 hours and 24 hours after anti-CD9 (n=6, p=0.01, two-way ANOVA).

To test the hypothesis that inhibition of miR-148a could protect mice from thrombosis secondary to activation of platelets via FcγRIIA, anti-mouse CD9 antibody was used to induce HIT-like symptoms. Anti-CD9 Ab binds to platelet surface and lead to platelet activation by the interaction between its Fc part and FcγRIIA.[45] Both the anti-miR-148a and scrambled anti-miR treated groups showed a drop in platelet count one hour post anti-mCD9 antibody administration, due to the combination of intravascular platelet activation and splenic clearance.[45] At 3 hours and 24 hours, the platelet count recovered. miR-148a inhibition resulted in significantly less severe thrombocytopenia in comparison to the control group. (FIG. 8).

Figure 6A:
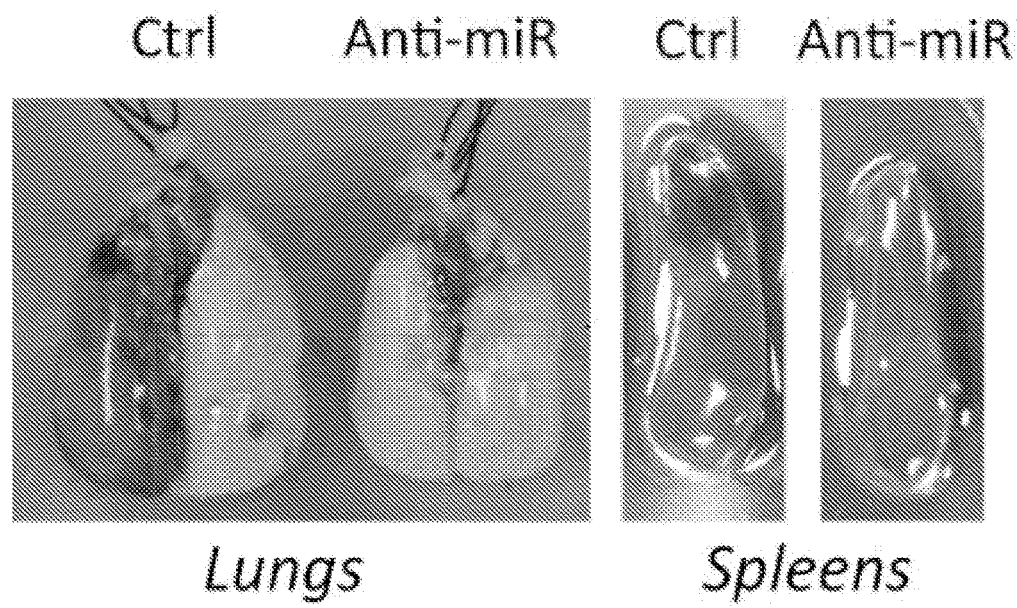
FIGS. 6A-D show the inhibition of miR-148a in vivo is protective against FcγRIIA-mediated thrombosis.
Figure 6B:
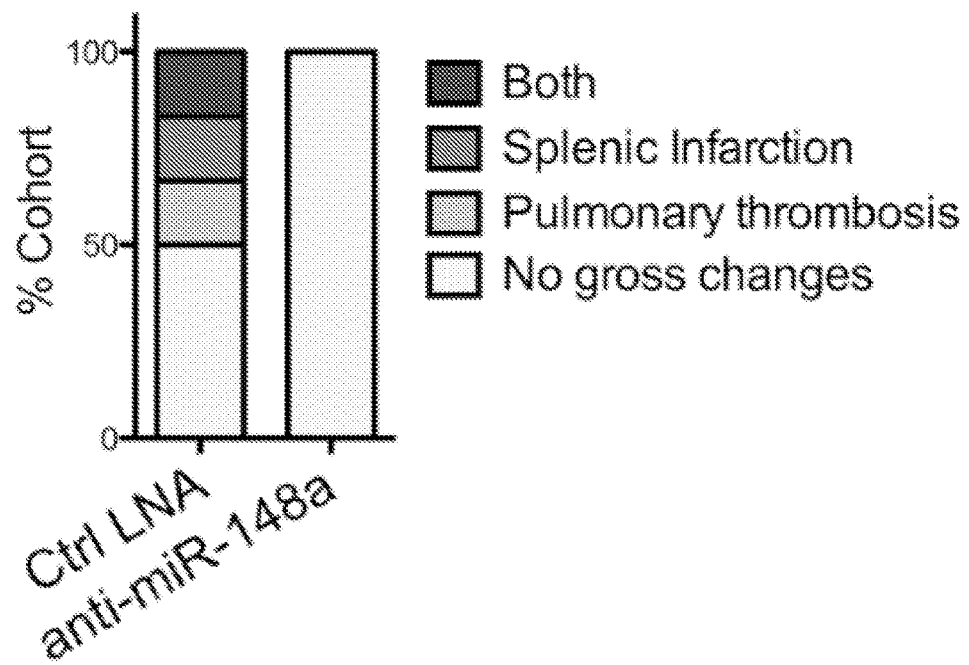
Figure 6C:
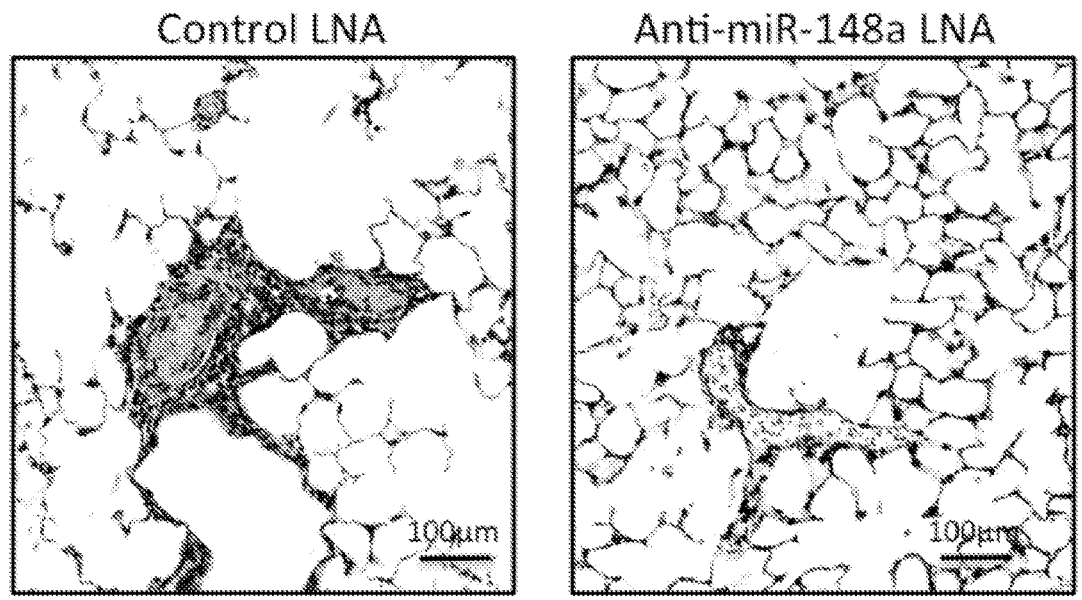
Figure 6D:
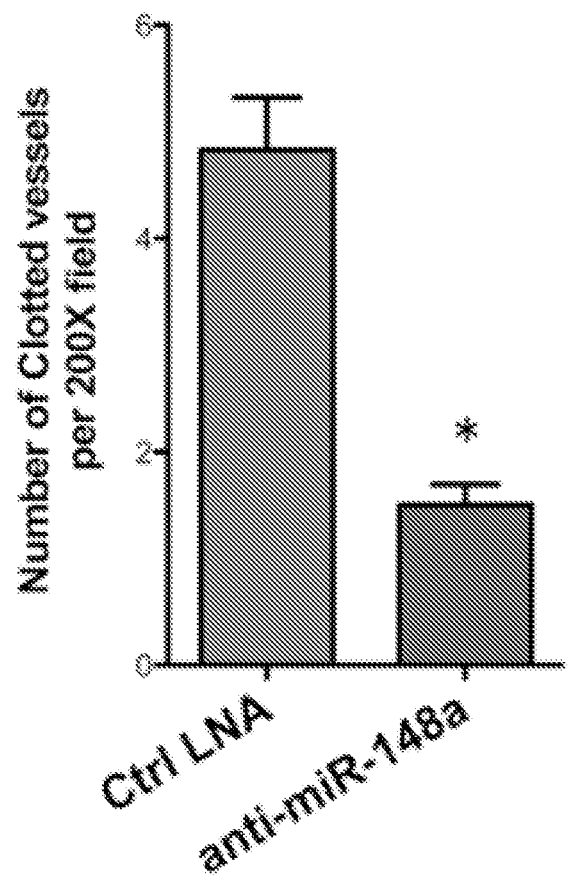
Figure 7:
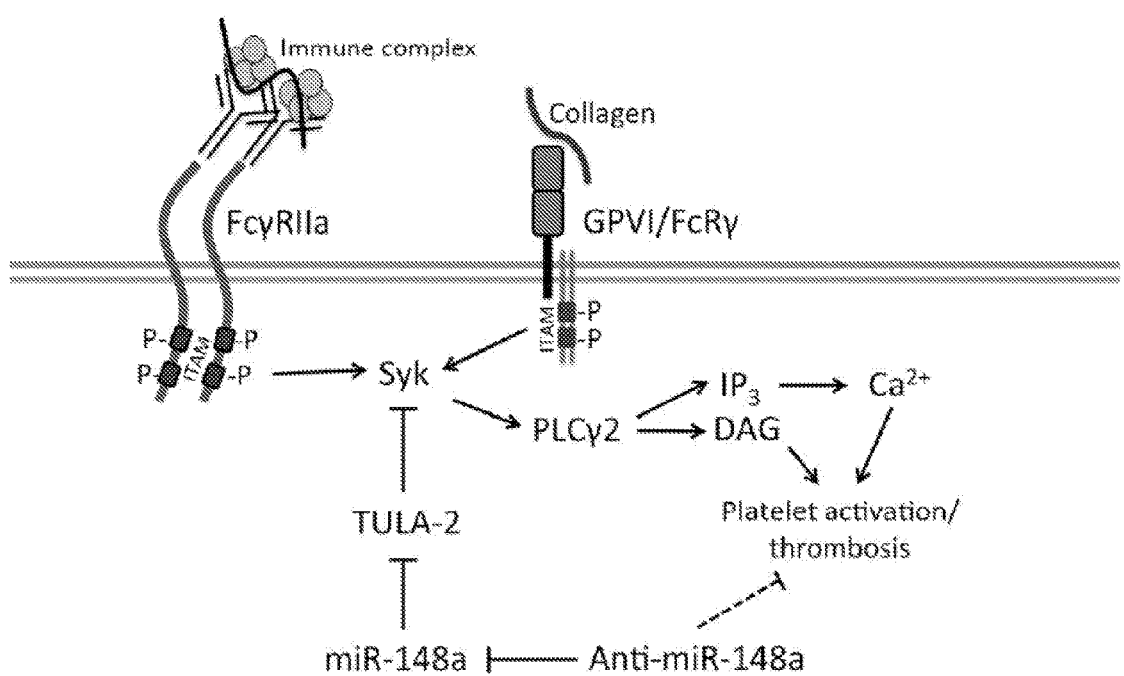
FIG. 7 is a schematic representation of the mechanism of the anti-thrombosis effect by miR-148a inhibition. This depicts the ITAM-Syk pathway and the proposed role of TULA-2, miR-148a, and anti-miR-148a. Anti-miR-148a indirectly ameliorates ITAM-Syk-mediated platelet activation by up-regulating TULA-2 expression, which further inactivates Syk and its downstream effectors. PLCγ2: phosphoinositide-specific phospholipase Cγ2. IP3: Inositol trisphosphate. DAG: diacylglycerol.

At the gross pathological level, pulmonary thrombosis and spleen infarction are well-established features of this model.[14] Upon examination, control anti-miR-treated mice showed more gross pathological changes than the anti-miR-148a group. Specifically, 3 out of 6 control mice had visibly evident thrombosis, while none out of 6 miR-148a-inhibited mice exhibited gross pathological changes (FIG. 6A, B). Additionally, histologic changes of the lungs were examined by light microscopy. Control anti-miR treated mice manifested diffuse thrombosis with platelet/fibrin deposition in the lung vasculature. In comparison, anti-miR148a treated mice displayed significantly reduced thrombi, as measured by thrombus-per-200× field (FIG. 6C, D). All together, these data points to a protective effect of miR-148a inhibition on FcγRIIA-mediated thrombosis in vivo. A possible mechanism of action of anti-miR-148a is indicated (FIG. 7).

Therefore, in preferred embodiments, anti-miR-148a can be used as a negative regulator of platelet activation and thrombosis via FcγRIIA. Anti-miR-148a increases the levels of platelet TULA-2, a protein tyrosine phosphatase. TULA-2, which has higher expression level in FcγRIIA hypo-responders, was previously shown to regulate T cell signaling, bone remodeling and the GPVI pathway in murine platelets.[18,20,46,47]

Accordingly, preferred methods of treating thrombosis include use of an LNA-based microRNA inhibition mechanism or other anti-miR chemistry, such as antagomir or chemistries that modify the base, the 5' end the 3' end, and/or the linkages. The options and chemistries for forming these chains of nucleotides are known to one of ordinary skill in the art. The LNA-based microRNA mechanism is proven to be safe, potent, and applicable in human therapy.[25,33] Indeed, several microRNA are utilized in pharmaceutical compositions to treat several ailments and diseases. For example, miR-208 is related to heart failure; miR-103/107 are related to metabolism; miR-122 is related to HCV; miR-155 is related to inflammation; miR-21 is related to fibrosis; miR-33 is related to atherosclerosis; miR-15 is related to cardiac repair; miR-451 is related to MPD; and miR-92a is related to neoangiogenesis. Accordingly, pharmaceutical compositions and administration of microRNA is a proven mechanism to modify chemical and cellular function in the body.

In a preferred embodiment, a 10-15 long nucleotide anti-miR-148a-3p (SEQ ID Nos: 19-24) is administered to a patient, wherein the anti-miR is suitable for reducing platelet activation in said patient, wherein the reduction in platelet activation provides for a corresponding reduction in thrombosis. The platelet activation is reduced through a negative regulator mechanism via an increase in the level of a protein that is a negative regulator of platelet activation.

FIG. 4B provides detail of an experiment using SEQ ID NO: 24 in in vivo experiments. qRT-PCR revealed that the anti-miR was effectively taken up by murine bone marrow and spleen, as demonstrated by greater than 96% miR-148a inhibition (FIG. 4B). In humans, miR-148a is highly expressed in megakaryocytes, platelets, granulocytes, erythrocytes, but less well expressed in other cells.[49] miR-148a has been associated with gastrointestinal cancers,[50,51] HIV infection,[52,41] and Th1-cell survival.[53] However, its role in megakaryocyte/platelet function has not been reported.

Therefore, in a preferred embodiment, a method of treating a patient with an anti-miR utilizes a treatment cycle of between 1 day and 365 days. In preferred embodiments, the treatment cycle is between 1 day and 180 days, between about 3 and 60 days, and 3 and 28 days. A cycle can also be defined as long as the injection of the anti-miR manifests on the target. Preferred embodiments utilize a dosing protocol, wherein the anti-miR is administered every day, on alternative days, or on the first 3 of 5 days, or of the first 3 days of a treatment cycle. Indeed, the anti-miR provides for a stable material that may be administered early in a treatment cycle and be maintained in the body for more than 30 days. Accordingly, a single dose may allow for the anti-miR to continue to manifest on the target well after the administration to the patient. Once a treatment cycle is completed, a new cycle can begin and the cycle can be repeated as in the prior cycle, or modified to fit the patient's needs. Accordingly, this provides that a patient may receive several bolus administrations during a brief period of 1-7 days, but have efficacy for at least 28 days The duration of treatment, will not likely have significant effects on tumorigenesis, giving that inhibition of miR-148a is not permanent. Indeed, this was confirmed in anti-miR treated mice experiments. Furthermore, no effects of anti-miR-148a treatment on HEL cell proliferation compared with scrambled control were detected in any of the studies performed herein.

Figure 10:
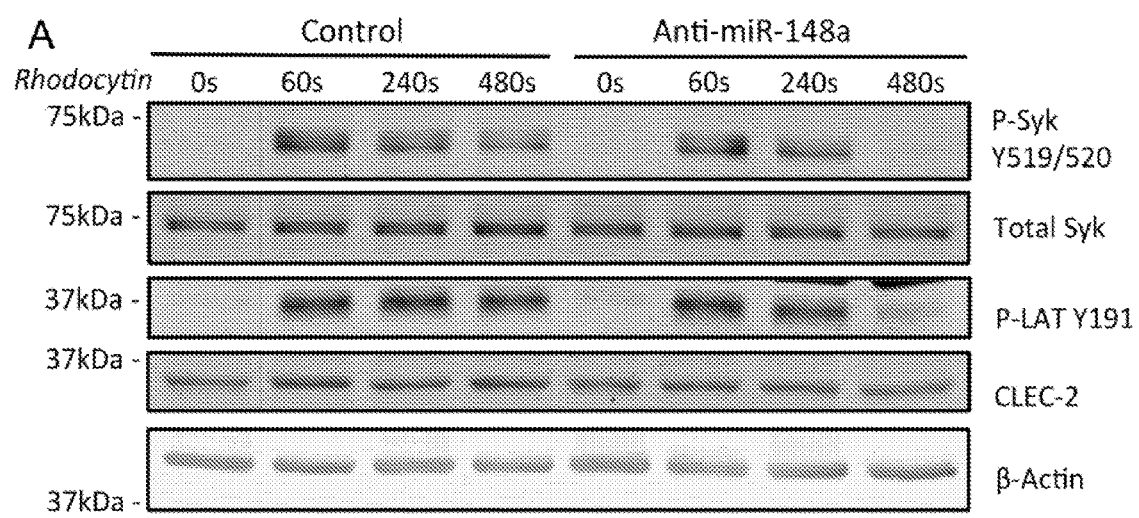
FIG. 10 depicts the Western blot on phospho-Syk Y519/520, total Syk, phospho-LAT Y191, CLEC-2 and beta-actin in 30 nM rhodocytin-treated murine platelets. Figure is representative of three experiments.
Figure 11A:
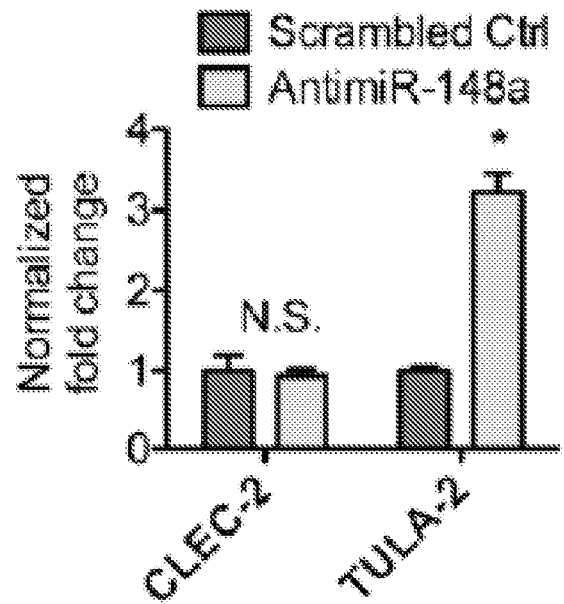
FIGS. 11A-B depicts the quantification of CLEC-2, TULA-2 and normalized P-Syk Y519/520 in control or anti-miR-148a treated murine platelets treated with 2 µg/mL IV.3+8 µg/mL GAM or 30 nM rhodocytin at 480 s time point (n=3, *P<0.05).
Figure 11B:
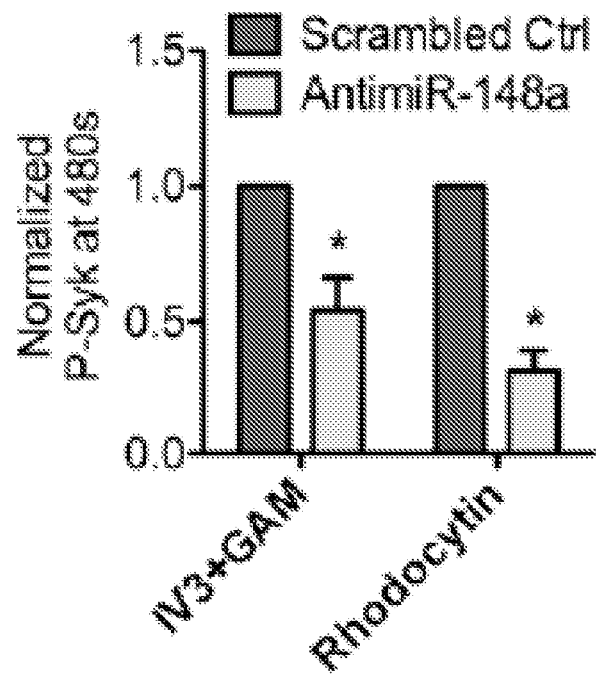
Figure 11:
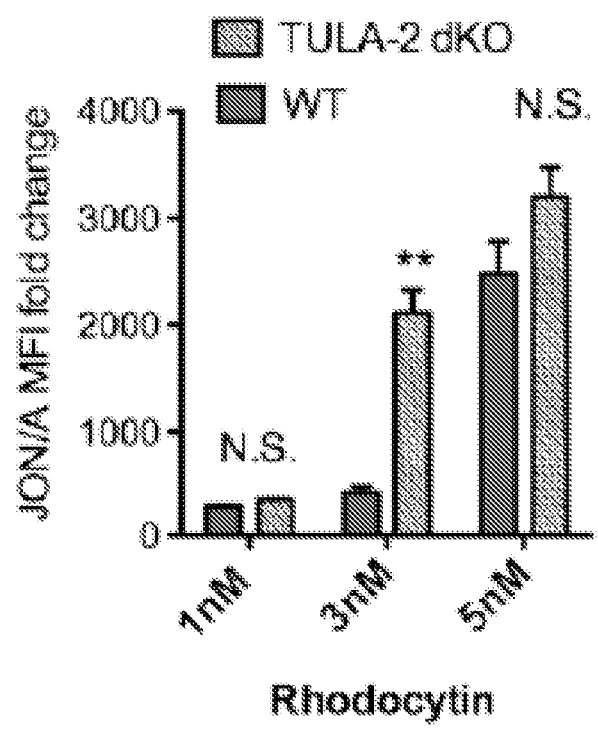
FIG. 11C illustrates the washed platelets from TULA-2 knockout (KO) or wild-type (WT) mice were treated with indicated concentration of rhodocytin without calcium under non-stirring condition. Integrin activation was analyzed as JON/A mean fluorescent intensity (MFI) fold change. (N=3, **P<0.005 for 3 nM rhodocytin).

In contrast, thrombin-mediated calcium influx did not show significant difference between the two experimental conditions. The ITAM-specific differential activation indicates TULA-2 up-regulation is the specific mediator for reduced thrombosis by anti-miR-148a. Syk plays a critical role in vascular injury response and thrombosis, as demonstrated by strong anti-thrombotic effects in vivo by Syk inhibitors.[6,61] Upregulation of TULA-2 by anti-miR-148a acts as a Syk inhibitor (FIG. 10 and FIG. 11A, 11B). Furthermore, platelets from TULA-2 double knockout mice showed increased integrin activation by 3 nM rhodocytin treatment compared with wild-type mice (FIG. 11C). Accordingly, it can be speculated that with multiple phosphate groups to be removed on active Syk, the amount of Syk phosphatase, TULA-2, is rate-limiting. Therefore, upregulation of TULA-2 by three fold (FIG. 4C, FIGS. 11A-B) provides a mechanism for significant effects on platelet activation and thrombosis.

Accordingly, the use of anti-miRNA therapeutics in a method of treatment approach to regulate platelet reactivity in vivo provides for novel mechanisms to treat thrombosis. A preferred mechanism reduces FcγRIIA-mediated thrombosis by inhibitying syk activity. This is achieved by increasing TULA-2 levels in platelets through inhibition of miR-148a levels in the body. The inhibition is achieved through administration of an antisense oligonucleotide against the miRNA 148a. Indeed, these Locked Nucleic Acids (LNA), are relatively small and simple modified oligonucleotides and having a high affinity and a high in vivo stability. Accordingly, development of these novel materials and pharmaceutical compositions containing the same provides for avenues to achieve a reduction of thrombosis.

Figure 12:
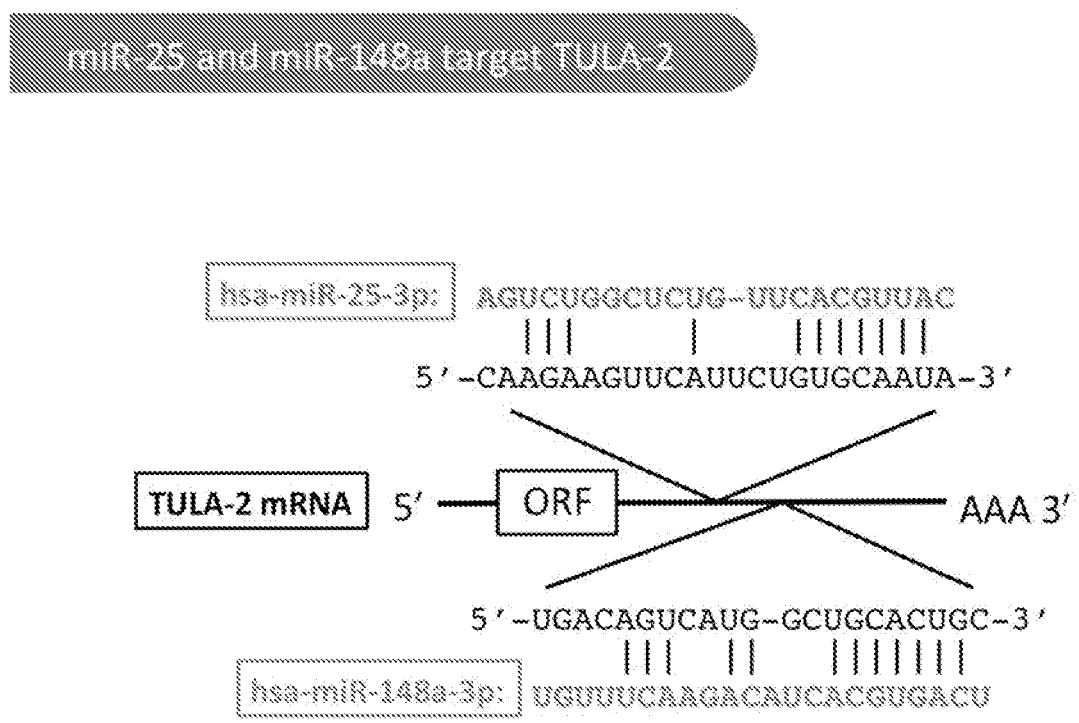
FIG. 12 depicts miR-25 (SEQ ID No: 7) and miR-148a (SEQ ID No: 1) targeting TULA-2 at different points (see SEQ ID Nos: 26 and 27).

However, it is not simply miR-148a that may be modified to achieve and regulate platelet formation and a corresponding reduction in thrombosis. miR-25, like miR-148a targets TULA-2. The location of these sequences is depicted in FIG. 12. Mouse and Human miR-25 are highly conserved having a sequence 5'-CAUUGCACUUGUCUCGGUCUGA-3' (SEQ ID No. 7). Other microRNA may also play a role in platelet activation and thrombosis. FIG. 12 further depicts—miRNA regulation is one of the possibilities that TULA-2 is differentially expressed. A multiple miRNA predication program was used to screen for miRNAs that are both highly expressed in platelets and can target TULA-2. In addition to miR-148a, it revealed miR-25 as a target for development. The schematic representation in FIG. 12 depicts the interaction between these two miRNAs and TULA-2 3' untranslated region.

Figure 13:
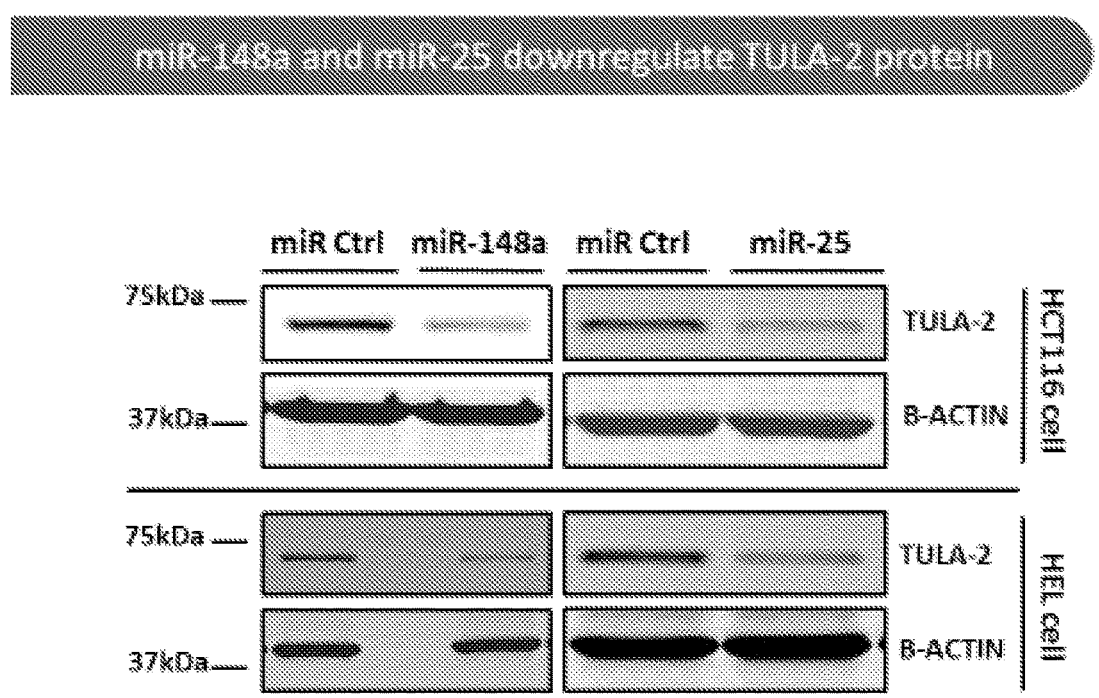
FIG. 13 depicts miR-148a and miR-25 downregulating TULA-2 protein.

Indeed, both miR-148a and miR-25 downregulate TULA-2 protein, as depicted in FIG. 13. To verify the interaction, miR-148a or miR-25 were overexpressed in HCT 116 dicer low cells as well as HEL cells. Overexpression of the miRNA lead to downregulated TULA-2 level as depicted in FIG. 13.

Figure 14:
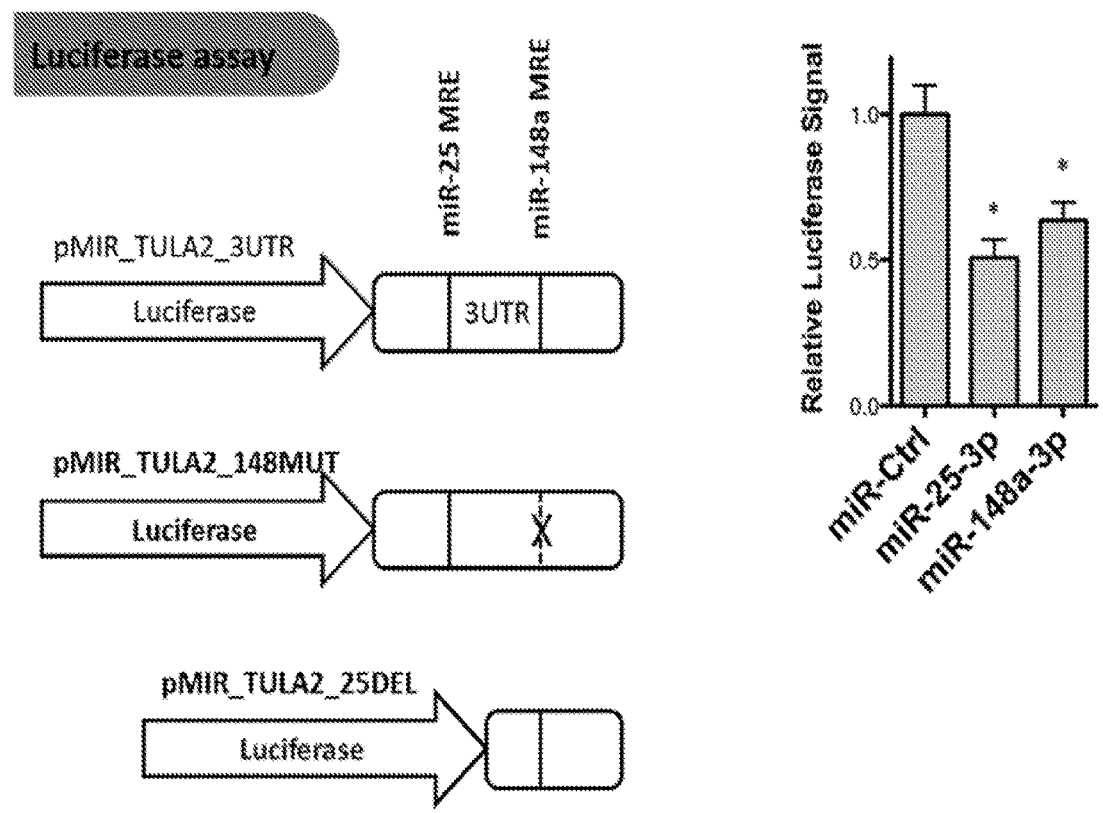

FIG. 14 depicts the use of a luciferase assay to further investigate the exact sites of interaction between miRNAs and TULA-2. First a 400 bp region of human TULA-2 3'UTR was cloned containing both miR-25 and miR-148a response elements into the luciferase 3'UTR in a pMIR report vector. miR-25 or miR-148a cotransfection with the vector resulted in decreased luciferase signal produced in HCT cells compared with control miRNA, suggesting these two miRNAs can inhibit luciferase protein translation by binding to the vector.

Figure 15:
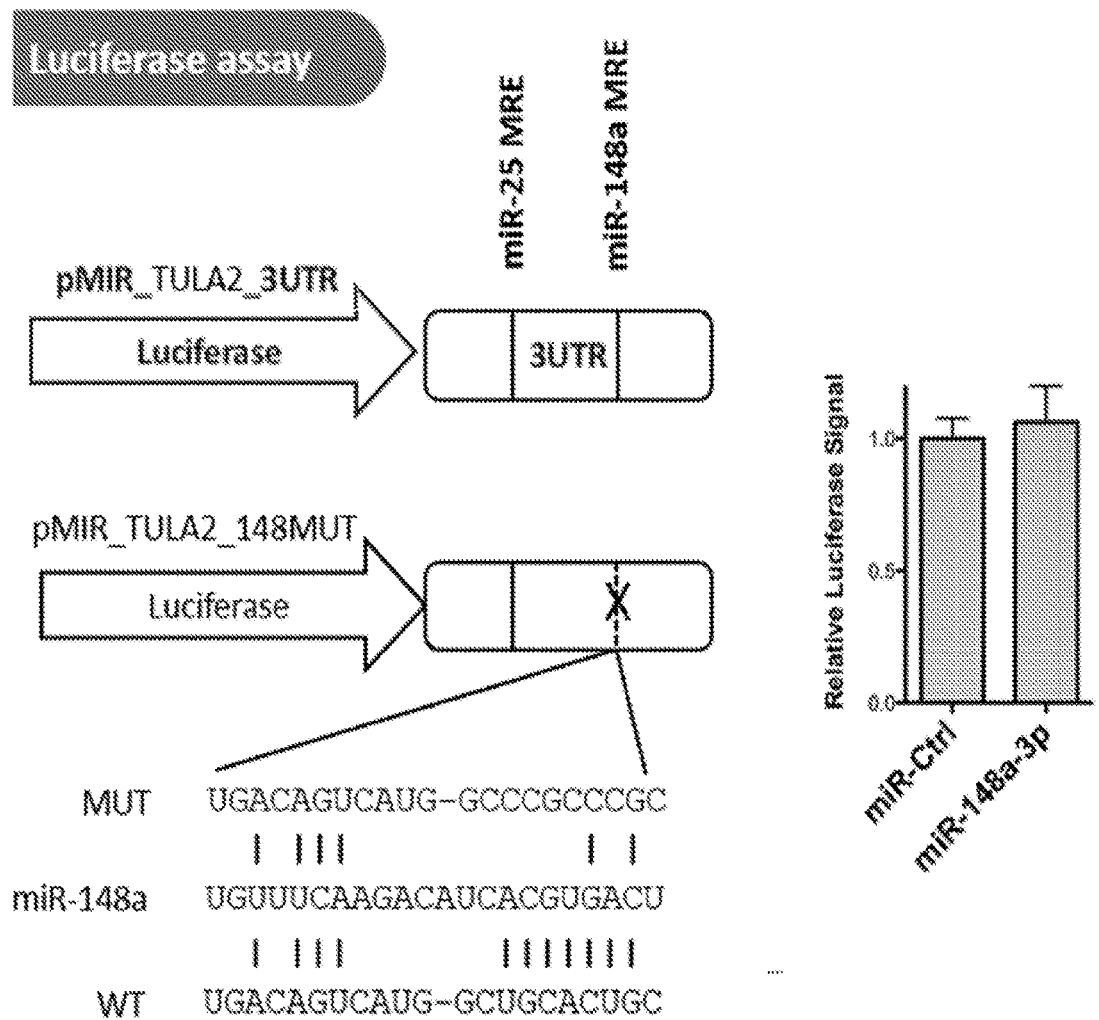

FIG. 15 When the potential binding seed region is mutated, the miR-148a's effect on luciferase signal is abolished. Suggesting that the exact interaction between TULA-2 3'UTR and miR-148a is mediated by the 7 nucleotide seed region.

Figure 16:
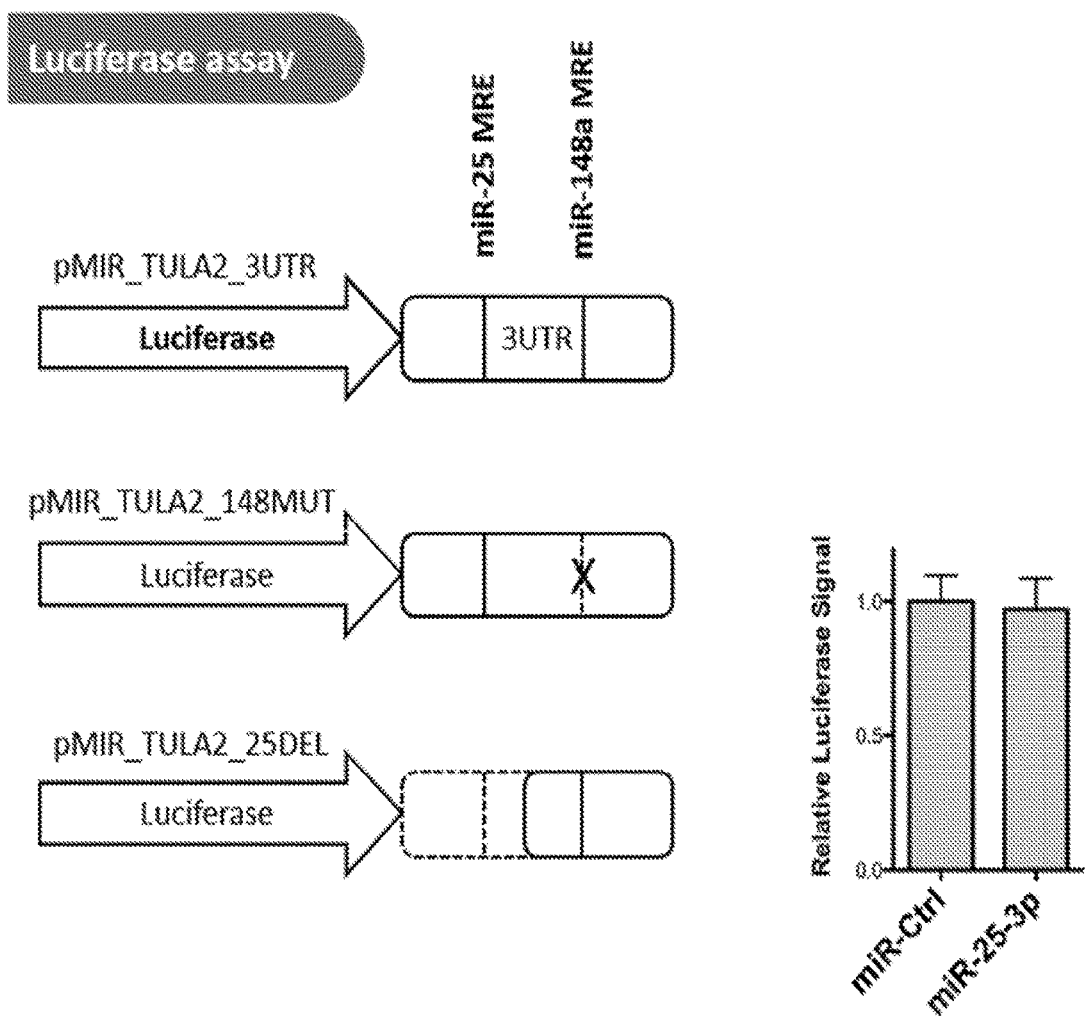
FIG. 16 depicts a further assay comparing miR-25 to a control.

FIG. 16 further depicts that for miR-25, the potential binding site was deleted but the miR-148a binding site remained. The results showed no difference between control miR and miR-25. This data suggests that the suspected binding site on TULA-2 3'UTR and miR-25 is responsible for the interaction. miR-25 and miR-148a have targets at different binding sites on TULA-2, as depicted in FIG. 12. Accordingly, in a preferred embodiment, The binding sites for miR-25 and miR-148a are on TULA-2, as depicted in FIG. 12. Therefore, administration of each anti-miR would not lead to binding competition at the two sites. Accordingly, in a preferred embodiment, a pharmaceutical composition comprises two anti-miR, one corresponding to miR-25 and one to miR-148a. This provides that two different anti-miR can be administered to reduce platelet activation. In certain embodiments, the combination of the two anti-miR may provide a synergistic effect such that suitable doses may be advantageously administered to a patient at a reduced rate as compared to single anti-miR. Preferred embodiments may use any of a 10-15 mer sequence of the anti-miR for miR-25 or miR-148a. FIG. 18 provides a detail of the six different suitable sequences for the anti-miR 148a having a length of 10, 11, 12, 13, 14, and 15 mer. These correspond to SEQ ID Nos: 19 to 24. The corresponding specific sequences of 10-15 mer for anti-miR-25 are not individually shown, but can be deduced from the 15 mer sequence depicted by SEQ ID no: 32, in FIG. 17, wherein the zero or up to five of the underlined nucleotides can be added to the 10 mer sequence that is not underlined.

Computational data provides the ability to test and predict some miR and corresponding anti-miR for effect against platelet activation. There are literally hundreds of miR that provide some potential overlap to TULA-2 and would predictably affect platelet activation. However, in practice, only a very small number of these miR provide any actual effects when tested. Accordingly, computational biology provides little help to one of ordinary skill in the art when attempting to predict suitable miR.

Accordingly, to date, experimentation is the only suitable manner in which to identify miR that have effects on platelet activation. FIG. 17 depicts a list of nine different miRs that affect TULA-2. In addition to miR-148a and miR-25 as previously disclosed, these seven additional miRs can be targeted alone, or in conjunction with one another, to affect platelet activation. As depicted in FIG. 17, the anti-miR is depicted as a 15 mer sequence, wherein the suitable anti-miR for administration may include between 10 and 15 nucleotides in SEQ ID Nos 29-34.

In developing a composition for treating of the four major classes of human thrombotic disorders, treatment with an anti-miR can regulate the platelet activation in the patient, thereby preventing thrombosis or reducing the occurrence of thrombosis as compared to an untreated control. Accordingly, anti-miRs can be utilized to bind and modify the activation of platelets and directly modify the body to reduce the formation of thrombus.

As anti-miRs work by binding to a particular binding site, it is possible for a sequence to be highly homologous, but not identical to a binding site and still provide the necessary effect. Accordingly, in certain embodiments, an anti-miR having a sequence that corresponds to 90% of the sequence of miR-148a or miR-25 is suitable as a composition to effect treatment. Therefore, in certain embodiments, the activation platelet cells can be modified by administering an anti-miR that is at least about 90% identical to SEQ ID: Nos: 19-24 or SEQ ID Nos: 29-34), each of which correspond to and will bind to the corresponding miR. The effect of the binding thereby increases the amount of TULA-2 protein which downregulates platelet activation.

However, by reducing the sequence to 90%, instead of matching all sequences of the miR, selectivity to the binding site may be significantly reduced. Accordingly, in preferred embodiments, an anti-miR of between 10 and 15 nucleotides is administered to a patient in need thereof, wherein the sequences have a 100% match with the corresponding miR of a length of between 10 and 15 nucleotides as depicted by FIG. 17 and SEQ ID Nos: 19-24 and 29-34.

Formulation of the anti-miRs described herein can be formulated by one of ordinary skill in the art. The anti-miR molecules can be administered to a patient via known suitable routes of administration, including orally, parenteral, buccal, ophthalmic, rectal, or other routes of administration as appropriate. Those of ordinary skill in the art are capable of formulating an appropriate pharmaceutical composition comprising the anti-miR molecules with appropriate excipients and pH to provide for safe administration of the compositions.

In certain embodiments, it may be advantageous to administer the anti-miR locally to target a particular thrombus or area of concern for thrombus formation. However, systemic administration is a suitable and preferred route of administration so as to prevent the formation of thrombus in any area of the body. Therefore, a preferred embodiment comprises administering to a subject in need thereof, an effective amount of a nucleic acid comprising the complement of the nucleotide sequence of miR-148a, so as to bind to these microRNA.

In further preferred embodiments, the anti-miR is selected from the group consisting of miR-148a-3p, 106a-5p, 150-5p, 199a/b-3p, 21-5p, 24-3p, 25-3p, 342-3p, and 93-5p or combinations thereof. The anti-miR is a sequence of between 10 and 15 nucleotides in SEQ ID Nos; 24 and 29-34, and identified in FIG. 17. Accordingly, any of the sequences of 10 nucleotides, or including the 10 nucleotides and one or more of the underlined nucleotides in SEQ ID Nos: 24 and 29-34 can be suitably administered to a patient for reducing platelet activation.

EXAMPLES

Whereas particular embodiments of this invention have been described above for purposes of illustration, it will be evident to those skilled in the art that numerous variations of the details of the present invention may be made without departing from the invention. The following examples are intended to provide for non-limiting examples as understood by one of ordinary skill in the art.

Material and Methods

Antibodies and Reagents:

Antibodies against human CD9 (Beckman Coulter Inc., Clone Alb6, mIgG$_1$), murine CD9 (BD Pharmingen, clone KMC8, rat IgG$_{2a}$), human FcγRIIA (clone IV.3, StemCell Technologies), human total Syk (clone 4D10, Santa Cruz Biotech), human phospho-Syk Y323 (Cell Signaling), human phospho-Syk Y525/526 (murine Y519/520) (Cell Signaling), murine phospho-LAT Y191 (Millipore), PE-labeled anti-mouse integrin α$_{IIb}$β$_3$ (clone JON/A, Emfret), goat anti-mouse IgG Fab'$_2$ (Santa Cruz Biotech), Fluo-4-AM (Life Technologies), thrombin (Chrono-PAR), collagen-related peptide (CRP, from Dr. Richard Farndale) were purchased. Anti-TULA-2 antibody was described previously.[34]

Cell Lines:

HEL 92.1.7 human erythroleukemia cells (ATCC, Manassas, Va., USA) were grown in RPMI-1640 (Gibco BRL, Rockville, Md., USA) media supplemented with 10% fetal calf serum (Atlanta Biologicals, Norcross, Ga., USA), 100 units/mL penicillin, and 100 μg/mL streptomycin. HCT116-Dicer-KO 2 cells were previously described.[35]

Mouse Model for HIT:

FcγRIIA transgenic mice (B6IIA) were created as previously described.[5] All mice are on the 100% C57BL/6 strain background. TULA-2 knock-out (KO) mice were described previously.[17] All animals were maintained at Thomas Jefferson University animal facility, which is approved by the Association for Assessment and Accreditation of Laboratory Animal Care (AAALAC) International. All protocols for using experimental mice were approved by the Institutional Animal Care and Use Committee of Thomas Jefferson University.

Human Platelet RNA and eXpression-1 (PRAX-1) Study:

Recruitment of the donors, whole blood collection, platelet isolation, aggregation by anti-CD9 antibody and platelet RNA profiling were done as previously described.[13,35] briefly, platelet rich plasma aggregation assay via FcγRIIA was conducted on 154 human healthy donors as part of the PRAX-1 study.

Murine Platelet Isolation:

Murine platelet isolation was previously described.[14]

siRNA and miRNA Overexpression:

200 nM TULA-2 siRNA, scrambled control siRNA (GE Dharmacon), 60 nM hsa-miR-148a-3p mirVana Mimics or control scrambled microRNA mimics (Life Technologies) were transfected into $2\times10^6$/mL HEL cells using Amaxa Nucleofector II device (Lonza) and Nucleofector Kit V (Lonza) following the company's protocol. Protein or RNA was extracted and analyzed 48 hours post-transfection.

TULA-2 Gene Luciferase Reporter Assay:

A region from TULA-2 3' untranslated regions (3'UTR) consisting of 113 base-pairs upstream and 93 base-pairs downstream of the potential binding site of miR148a-3p was cloned into the pMIR-REPORT luciferase construct (Life Technologies). The mutant construct of TULA-2 3'UTR was created by using a QuikChange Site-Directed Mutagenesis Kit (Agilent Technologies). In the TULA-2 3'UTR mutant, the nucleotide sequence of the seed region was mutated from 5'TGCACT3' to 5' CCGCCC3'. The reporter plasmids (60 ng), beta-gal vector (50 ng), and miRNA or scrambled control (Ambion, 60 nM final concentration) were transfected into HCT-116-Dicer KO 2 cells in triplicates with Lipofectamine LTX and PLUS reagent. Data was obtained and normalized by Luciferase Assay System and beta-galactosidase enzyme assay system (Promega) using LUMIstar OPTIMA luminescence microplate reader (BMG Labtech).

Anti-miR-148a Treatment In Vivo:

Custom-designed anti-miR-148a-3p locked nucleic acid (LNA) was purchased from Exiqon. Siblings of FcγRIIA transgenic mice at the same age were assigned into scrambled LNA or anti-miR-148a LNA treatment groups. Mice were treated with 25 mg/kg LNA in sterile saline on alternate days for five doses via intraperitoneal injection. Blood counts were measured by the Hemavet HV950 (Drew Scientific, Inc. Dallas, Tex.).

Integrin $\alpha_{IIb}\beta_3$ Activation Assay:

Murine platelets were washed and resuspended in Tyrode's buffer with 1 mM $CaCl_2$ and 0.35% BSA to $5\times10^7$ platelets/mL. Various concentrations of collagen related peptide (CRP) or IV.3+GAM were used to activate platelets in the presence of 2 μg/mL JON/A-PE, an antibody that binds to activated form of $\alpha_{IIb}\beta_3$. Fluorescent intensity was measured by a BD Accuri C6 flow cytometer after 10 minutes.

Calcium Mobilization Assay:

$1\times10^6$ washed murine platelets were labeled with 2.5 μg/mL Fluo-4-AM for 10 minutes at 37° C. Platelets were analyzed for fluorescence intensity with 1 mM $CaCl_2$ for 1 minute to establish baseline. At 60 seconds, indicated concentrations of CRP and IV.3+GAM were added and calcium mobilization was measured over a period of 5 minutes by a BD Accuri C6 flow cytometer. The calcium fold change data in the plot represents the calcium concentration at every second divided by basal calcium concentration.

FcγRIIA-Mediated Thrombosis Model:

Under anesthesia by inhaling isoflurane, mice were injected with the anti-mouse CD9 antibody into the retro-orbital sinus at a concentration of 2.5 mg/kg body weight. Livers, spleens, and lungs were obtained by laparotomy and thoracotomy and were stored immediately in RNAlater RNA stabilization reagent (Qiagen). Bone marrows were collected from the tibias. Total RNA was isolated from tissues by lysing with TRIzol reagent (Invitrogen) or by RNeasy mini RNA purification kit (Qiagen). Reverse transcription PCR was performed, and target RNAs were quantified by qRT-PCR.

H&E Staining:

Inflated lungs were extracted and fixed in 10% formalin for 24 hours. Cryosection and H&E staining were prepared by the Veterinary Medical Diagnostic Lab at University of Missouri, College of Veterinary Medicine. Images were captured with Carl Zeiss Axio Observer Z1 microscope.

Statistics:

Results were reported as mean±standard error of the mean (SEM). Statistical significance was determined by 2-tailed Student t-test or two-way analysis of variance. A p value <0.05 was considered significant.

REFERENCES

1. Martel N, Lee J, Wells P S. Risk for heparin-induced thrombocytopenia with unfractionated and low-molecular-weight heparin thromboprophylaxis: a meta-analysis. *Blood.* 2005; 106(8):2710-2715.
2. Schmitt B P, Adelman B. Heparin-associated thrombocytopenia: a critical review and pooled analysis. *Am J Med Sci.* 1993; 305(4):208-215.
3. McKenzie S E, Sachais B S. Advances in the pathophysiology and treatment of heparin-induced thrombocytopenia. *Current opinion in hematology.* 2014; 21(5):380-387.
4. Reilly M P, Taylor S M, Hartman N K, et al. Heparin-induced thrombocytopenia/thrombosis in a transgenic mouse model requires human platelet factor 4 and platelet activation through FcγRIIA. *Blood.* 2001; 98(8):2442-2447.
5. McKenzie S E, Taylor S M, Malladi P, et al. The role of the human Fc receptor FcγRIIA in the immune clearance of platelets: a transgenic mouse model. *The Journal of Immunology.* 1999; 162(7):4311-4318.
6. Reilly M P, Sinha U, André P, et al. PRT-060318, a novel Syk inhibitor, prevents heparin-induced thrombocytopenia and thrombosis in a transgenic mouse model. *Blood.* 2011; 117(7):2241-2246.
7. Yanaga F, Poole A, Asselin J, et al. Syk interacts with tyrosine-phosphorylated proteins in human platelets activated by collagen and cross-linking of the Fc gamma-IIA receptor. *Biochem J* 1995; 311 (Pt 2):471-478.
8. Boylan B, Gao C, Rathore V, Gill J C, Newman D K, Newman P J. Identification of FcγRIIa as the ITAM-bearing receptor mediating αIIbβ3 outside-in integrin signaling in human platelets. *Blood.* 2008; 112(7):2780-2786.

9. Zhi H, Rauova L, Hayes V, et al. Cooperative integrin/ITAM signaling in platelets enhances thrombus formation in vitro and in vivo. *Blood.* 2013; 121(10):1858-1867.
10. Arepally G, McKenzie S E, Jiang X-M, Poncz M, Cines D B. FcγRIIA H/R131 polymorphism, subclass-specific IgG anti-heparin/platelet factor 4 antibodies and clinical course in patients with heparin-induced thrombocytopenia and thrombosis. *Blood.* 1997; 89(2):370-375.
11. Rollin Jrm, Pouplard C, Gratacap M-P, et al. Polymorphisms of protein tyrosine phosphatase CD148 influence FcγRIIA-dependent platelet activation and the risk of heparin-induced thrombocytopenia. *Blood.* 2012; 120(6):1309-1316.
12. Pamela S, Anna Maria L, Elena D, et al. Heparin-induced thrombocytopenia: The role of platelets genetic polymorphisms. *Platelets.* 2012; 24(5):362-368.
13. Simon L M, Edelstein L C, Nagalla S, et al. Human platelet microRNA-mRNA networks associated with age and gender revealed by integrated plateletomics. *Blood.* 2014; 123(16):e37-e45.
14. Stolla M, Stefanini L, André P, et al. CalDAG-GEFI deficiency protects mice in a novel model of FcγRIIA-mediated thrombosis and thrombocytopenia. *Blood.* 2011; 118(4):1113-1120.
15. Yeung J, Tourdot B E, Fernandez-Perez P, et al. Platelet 12-LOX is essential for FcγRIIa-mediated platelet activation. *Blood.* 2014; 124(14):2271-2279.
16. Tsygankov A Y. TULA-family proteins: A new class of cellular regulators. *Journal of cellular physiology.* 2013; 228(1):43-49.
17. Carpino N, Turner S, Mekala D, et al. Regulation of ZAP-70 activation and TCR signaling by two related proteins, Sts-1 and Sts-2. *Immunity.* 2004; 20(1):37-46.
18. Chen X, Ren L, Kim S, et al. Determination of the substrate specificity of protein-tyrosine phosphatase TULA-2 and identification of Syk as a TULA-2 substrate. *Journal of biological chemistry.* 2010; 285(41):31268-31276.
19. Newman T N, Liverani E, Ivanova E, et al. Members of the novel UBASH3/STS/TULA family of cellular regulators suppress T-cell-driven inflammatory responses in vivo. *Immunology and cell biology.* 2014; 92(10):837-850.
20. Thomas D H, Getz T M, Newman T N, et al. A novel histidine tyrosine phosphatase, TULA-2, associates with Syk and negatively regulates GPVI signaling in platelets. *Blood.* 2010; 116(14):2570-2578.
21. Nieswandt B, Watson S P. Platelet-collagen interaction: is GPVI the central receptor? *Blood.* 2003; 102(2):449-461.
22. Dumont B, Lasne D, Rothschild C, et al. Absence of collagen-induced platelet activation caused by compound heterozygous GPVI mutations. *Blood.* 2009.
23. Mócsai A, Ruland J, Tybulewicz V L. The SYK tyrosine kinase: a crucial player in diverse biological functions. *Nature Reviews Immunology.* 2010; 10(6):387-402.
24. Elmen J, Lindow M, Silahtaroglu A, et al. Antagonism of microRNA-122 in mice by systemically administered LNA-antimiR leads to up-regulation of a large set of predicted target mRNAs in the liver. *Nucleic acids research.* 2008; 36(4):1153-1162.
25. Vester B, Wengel J. LNA (locked nucleic acid): high-affinity targeting of complementary RNA and DNA. *Biochemistry.* 2004; 43(42): 13233-13241.
26. Rayner K J, Esau C C, Hussain F N, et al. Inhibition of miR-33a/b in non-human primates raises plasma HDL and lowers VLDL triglycerides. *Nature.* 2011; 478(7369): 404-407.
27. Marquart T J, Wu J, Lusis A J, Baldán Á. Anti-miR-33 therapy does not alter the progression of atherosclerosis in low-density lipoprotein receptor-deficient mice. *Arteriosclerosis, thrombosis, and vascular biology.* 2013; 33(3): 455-458.
28. Rayner K J, Sheedy F J, Esau C C, et al. Antagonism of miR-33 in mice promotes reverse cholesterol transport and regression of atherosclerosis. *The Journal of clinical investigation.* 2011; 121(121 (7)):2921-2931.
29. Wang X, Zhu H, Zhang X, et al. Loss of the miR-144/451 cluster impairs ischaemic preconditioning-mediated cardioprotection by targeting Rac-1. *Cardiovascular research.* 2012; 94(2):379-390.
30. Montgomery R L, Hullinger T G, Semus H M, et al. Therapeutic inhibition of miR-208a improves cardiac function and survival during heart failure. *Circulation.* 2011; 124(14):1537-1547.
31. Bhagat T D, Zhou L, Sokol L, et al. miR-21 mediates hematopoietic suppression in MDS by activating TGF-β signaling. *Blood.* 2013; 121(15):2875-2881.
32. Garchow B G, Encinas O B, Leung Y T, et al. Silencing of microRNA-21 in vivo ameliorates autoimmune splenomegaly in lupus mice. *EMBO molecular medicine.* 2011; 3(10):605-615.
33. Janssen H L, Reesink H W, Lawitz E J, et al. Treatment of HCV infection by targeting microRNA. *New England Journal of Medicine.* 2013; 368(18): 1685-1694.
34. Smirnova E V, Collingwood T S, Bisbal C, et al. TULA proteins bind to ABCE-1, a host factor of HIV-1 assembly, and inhibit HIV-1 biogenesis in a UBA-dependent fashion. *Virology.* 2008; 372(1):10-23.
35. Edelstein L C, Simon L M, Montoya R T, et al. Racial differences in human platelet PAR4 reactivity reflect expression of PCTP and miR-376c. *Nature medicine.* 2013.
36. Chen J, Dong J F, Sun C, et al. Platelet FcγRIIA HIS131ARG polymorphism and platelet function: antibodies to platelet-bound fibrinogen induce platelet activation. *Journal of Thrombosis and Haemostasis.* 2003; 1(2):355-362.
37. Arepally G, McKenzie S E, Jiang X M, Poncz M, Cines D B. Fc gamma RIIA H/R 131 polymorphism, subclass-specific IgG anti-heparin/platelet factor 4 antibodies and clinical course in patients with heparin-induced thrombocytopenia and thrombosis. *Blood.* 1997; 89(2):370-375.
38. Bachelot-Loza C, Saffroy R, Lasne D, Chatellier G, Aiach M, Rendu F. Importance of the FcgammaRIIa-Arg/His-131 polymorphism in heparin-induced thrombocytopenia diagnosis. *Thromb Haemost.* 1998; 79(3):523-528.
39. Buitrago L, Bhavanasi D, Dangelmaier C, et al. Tyrosine phosphorylation on spleen tyrosine kinase (syk) is differentially regulated in human and murine platelets by protein kinase C isoforms. *Journal of Biological Chemistry.* 2013; 288(40):29160-29169.
40. Miranda K C, Huynh T, Tay Y, et al. A pattern-based method for the identification of MicroRNA binding sites and their corresponding heteroduplexes. *Cell.* 2006; 126 (6):1203-1217.
41. Bennett J S. Structure and function of the platelet integrin αIIbβ3. *Journal of Clinical Investigation.* 2005; 115(12):3363.

42. Shattil S J, Kashiwagi H, Pampori N. Integrin signaling: the platelet paradigm. *Blood.* 1998; 91(8):2645-2657.
43. Calvete J J. On the structure and function of platelet integrin αIIbβ3, the fibrinogen receptor. *Experimental Biology and Medicine.* 1995; 208(4):346-360.
44. VARGA-SZABO D, Braun A, Nieswandt B. Calcium signaling in platelets. *Journal of Thrombosis and Haemostasis.* 2009; 7(7): 1057-1066.
45. Taylor S M, Reilly M P, Schreiber A D, Chien P, Tuckosh J R, McKenzie S E. Thrombosis and shock induced by activating antiplatelet antibodies in human FcγRIIA transgenic mice: the interplay among antibody, spleen, and Fc receptor. *Blood.* 2000; 96(13):4254-4260.
46. Back S H, Adapala N S, Barbe M F, Carpino N C, Tsygankov A Y, Sanjay A. TULA-2, a novel histidine phosphatase, regulates bone remodeling by modulating osteoclast function. *Cellular and Molecular Life Sciences.* 2013; 70(7):1269-1284.
47. Agrawal R, Carpino N, Tsygankov A. TULA proteins regulate activity of the protein tyrosine kinase Syk. *Journal of cellular biochemistry.* 2008; 104(3):953-964.
48. Fei Y, Webb R, Cobb B L, Direskeneli H, Saruhan-Direskeneli G, Sawalha A H. Identification of novel genetic susceptibility loci for Behcet's disease using a genome-wide association study. *Arthritis Research and Therapy.* 2009; 11(3):R66.
49. Teruel-Montoya R, Kong X, Abraham S, et al. MicroRNA Expression Differences in Human Hematopoietic Cell Lineages Enable Regulated Transgene Expression. *PloS one.* 2014; 9(7):e102259.
50. Chen Y, Song Y, Wang Z, et al. Altered expression of MiR-148a and MiR-152 in gastrointestinal cancers and its clinical significance. *J Gastrointest Surg.* 2010; 14(7): 1170-1179.
51. Zheng B, Liang L, Wang C, et al. MicroRNA-148a suppresses tumor cell invasion and metastasis by downregulating ROCK1 in gastric cancer. *Clin Cancer Res.* 2011; 17(24):7574-7583.
52. Kulkarni S, Savan R, Qi Y, et al. Differential microRNA regulation of HLA-C expression and its association with HIV control. *Nature.* 2011; 472(7344):495-498.
53. Haftmann C, Stittrich A B, Zimmermann J, et al. miR-148a is upregulated by Twist1 and T-bet and promotes Th1-cell survival by regulating the proapoptotic gene Bim. *European journal of immunology.* 2015.
54. Suzuki-Inoue K, Fuller G L, Garcia Á, et al. A novel Syk-dependent mechanism of platelet activation by the C-type lectin receptor CLEC-2. *Blood.* 2006; 107(2):542-549.
55. Hughes C E, Pollitt A Y, Mori J, et al. CLEC-2 activates Syk through dimerization. *Blood.* 2010; 115(14):2947-2955.
56. Lorenz V, Stegner D, Stritt S, et al. Targeted downregulation of platelet CLEC-2 occurs through Syk-independent internalization. *Blood.* 2015:blood-2014-2011-611905.
57. Suzuki-Inoue K, Inoue O, Ding G, et al. Essential in Vivo Roles of the C-type Lectin Receptor CLEC-2 EMBRYONIC/NEONATAL LETHALITY OF CLEC-2-DEFICIENT MICE BY BLOOD/LYMPHATIC MIS-CONNECTIONS AND IMPAIRED THROMBUS FORMATION OF CLEC-2-DEFICIENT PLATELETS. *Journal of Biological Chemistry.* 2010; 285(32):24494-24507.
58. Navarro-Núñez L, Langan S A, Nash G B, Watson S P. The physiological and pathophysiological roles of platelet CLEC-2. *Thromb Haemost.* 2013; 109(6):991-998.
59. Pollitt A Y, Poulter N S, Gitz E, et al. Syk and Src Family Kinases Regulate C-type Lectin Receptor 2 (CLEC-2)-mediated Clustering of Podoplanin and Platelet Adhesion to Lymphatic Endothelial Cells. *Journal of Biological Chemistry.* 2014; 289(52):35695-35710.
60. Bender M, May F, Lorenz V, et al. Combined in vivo depletion of glycoprotein VI and C-type lectin-like receptor 2 severely compromises hemostasis and abrogates arterial thrombosis in mice. *Arteriosclerosis, thrombosis, and vascular biology.* 2013; 33(5):926-934.
61. Andre P, Morooka T, Sim D, et al. Critical role for Syk in responses to vascular injury. *Blood.* 2011; 118(18): 5000-5010.

What is claimed is:

1. A method for reducing platelet activation comprising administering to a patient in need thereof an effective amount of an anti-miR having a corresponding miR having a binding site on TULA-2, wherein the binding of the anti-miR upregulates TULA-2 to mediate platelet activation in the body.

2. The method of claim 1, wherein the anti-miR corresponds to anti-miR-148a-3p, 106a-5p, 150-5p, 199a/b-3p, 21-5p, 24-3p, 25-3p, 342-3p, and 93-5p.

3. The method of claim 1 wherein the anti-miR corresponds to a sequence selected from the group consisting of SEQ ID Nos: 19-24 and 29-34.

4. The method of claim 1 further comprising at least two different anti-miRs selected from the group consisting of anti-miR-148a-3p, 106a-5p, 150-5p, 199a/b-3p, 21-5p, 24-3p, 25-3p, 342-3p, and 93-5p and combinations thereof.

5. The method of claim 4 where the at least two different anti-miRs are miR-25-3p and miR-148a-3p.

6. The method of claim 5 wherein the sequences for anti-miR-25-3p is a 10 to 15 nucleotide sequence of SEQ ID No; 32 and the sequence for anti-miR-148a-3p is selected from SEQ ID Nos: 19 to 24.

7. A method for treating thrombosis comprising administering to a subject in need thereof, an effective amount of an anti-miR capable of upregulating the level of a TULA-2 protein that is a negative regulator of platelet activation.

8. The method of claim 7, wherein the anti-miR corresponds to anti-miR-148a-3p, 106a-5p, 150-5p, 199a/b-3p, 21-5p, 24-3p, 25-3p, 342-3p, and 93-5p.

9. The method of claim 7 wherein the anti-miR corresponds to a sequence selected from the group consisting of SEQ ID Nos: 19-24 and 29-34.

10. The method of claim 7 further comprising at least two different anti-miRs selected from the group consisting of anti-miR-148a-3p, 106a-5p, 150-5p, 199a/b-3p, 21-5p, 24-3p, 25-3p, 342-3p, and 93-5p and combinations thereof.

11. The method of claim 10 where the at least two different anti-miRs are miR-25-3p and miR-148a-3p.

12. The method of claim 11 wherein the sequences for anti-miR-25-3p is a 10 to 15 nucleotide sequence of SEQ ID No; 32 and the sequence for anti-miR-148a-3p is selected from SEQ ID Nos: 19 to 24.

13. The method of claim 1 wherein said administering said effective amount of an anti-miR comprises administering to said patient an effective amount of an anti-miR for a treatment cycle of between 1 and 28 days.

14. The method of claim 13, wherein a cycle comprises administration of an anti-miR on a daily basis for the duration of the treatment cycle.

15. The method of claim 13, wherein a cycle comprises administration of at least three days, and wherein the anti-miR is administered every other day for the duration of the treatment cycle.

16. The method of claim 13, wherein a cycle is at least 7 days in duration, and wherein the cycle comprises administration of an anti-miR for three out of 7 days during a treatment cycle.

17. The method of claim 1 wherein said anti-miR is capable of inhibiting a corresponding miR wherein the inhibition down regulates the mRNA encoding for TULA-2 and causing a subsequent increase in the amount of mRNA encoding TULA-2, which downregulates platelet activation.

18. The method of claim 1, wherein said effective amount of an anti-miR is effective for reducing FcγRIIA-mediated thrombosis by inhibiting Syk activation by administering to a patient in need thereof an anti-miR against miRNA 148a-3p, wherein the inhibition of the miR-148a increases the TULA-2 levels in platelets in the body.

* * * * *